(12) United States Patent
Hornstein et al.

(10) Patent No.: US 8,734,759 B2
(45) Date of Patent: May 27, 2014

(54) METHODS OF DIAGNOSING AND TREATING MOTOR NEURON DISEASES

(75) Inventors: Eran Hornstein, Rehovot (IL); Alon Chen, Rehovot (IL); Sharon Haramati, Rehovot (IL); Elik Chapnik, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 13/132,923

(22) PCT Filed: Dec. 3, 2009

(86) PCT No.: PCT/IL2009/001148
§ 371 (c)(1),
(2), (4) Date: Jun. 5, 2011

(87) PCT Pub. No.: WO2010/064248
PCT Pub. Date: Jun. 10, 2010

(65) Prior Publication Data
US 2011/0239312 A1    Sep. 29, 2011

Related U.S. Application Data

(60) Provisional application No. 61/193,535, filed on Dec. 5, 2008.

(51) Int. Cl.
*C12Q 1/68* (2006.01)
*C12N 15/113* (2010.01)
*A61P 25/02* (2006.01)

(52) U.S. Cl.
USPC ............... 424/9.1; 435/6.1; 514/44 R; 506/9

(58) Field of Classification Search
CPC ................ G01N 2800/28; G01N 2800/50
See application file for complete search history.

(56) References Cited

U.S. PATENT DOCUMENTS

| | | | |
|---|---|---|---|
| 8,071,562 B2 * | 12/2011 | Bader et al. ............ | 514/44 A |
| 2006/0247193 A1 * | 11/2006 | Taira et al. ............ | 514/44 |
| 2008/0176766 A1 | 7/2008 | Brown et al. | |
| 2009/0246136 A1 | 10/2009 | Williams et al. | |

FOREIGN PATENT DOCUMENTS

| WO | WO 2007/016548 | 2/2007 |
|---|---|---|
| WO | WO 2010/064248 | 6/2010 |

OTHER PUBLICATIONS

Krichevsky A M et al: A microRNA array reveals extensive regulation of microRNAs during brain development; RNA, 2003, 9:1274-128.*
Rory Johnson et al., A microRNA-based gene dysregulation pathway in Huntington's disease. Neurobiology of Disease 29 (2008) 438-445.*
Packer et al., The Bifunctional microRNA miR-9/miR-9* Regulates REST and CoREST and Is Downregulated in Huntington's Disease. The Journal of Neuroscience, Dec. 31, 2008 o 28(53):14341-14346.*
Communication Pursuant to Article 94(3) EPC Dated May 16, 2012 From the European Patent Office Re. Application No. 09806203.7.
Communication Relating to the Results of the Partial International Search Dated Jul. 28, 2010 From the International Searching Authority Re. Application No. PCT/IL2009/001148.
International Preliminary Report on Patentability Dated Jun. 16, 2011 From the International Bureau of WIPO Re. Application No. PCT/IL2009/001148.
International Search Report and the Written Opinion Dated Oct. 8, 2010 From the International Searching Authority Re. Application No. PCT/IL2009/001148.
Deo et al. "Detection of Mammalian MicroRNA Expression by in Situ Hybridization With RNA Oligonucleotides", Developmental Dynamics: An Official Publication of the American Association of Anatomists, XP002587629, 235(9): 2538-2548, Sep. 2006. p. 2541, § 4, p. 2543, § 4.
Johnson et al. "A MicroRNA-Based Gene Dysregulation Pathway in Huntington's Disease", Neurobiology of Disease, XP002587620, 29: 438-445, Nov. 13, 2007. p. 438, col. 2, p. 439, Table 1, p. 440, col. 1, p. 441, Fig.4.
Krichevsky et al. "A MicroRNA Array Reveals Extensive Regulation of MicroRNAs During Brain Development", RNA, XP002587630, 9(10): 1274-1281, Oct. 2003. p. 1274, col. 2, p. 1275, col. 1, p. 1276, col. 2, p. 1277, col. 2.
Figlewicz et al. "Variants of the Heavy Neurofilament Subunit Are Associated With the Development of Amytrophic Lateral Sclerosis", Human Molecular Genetics, 3(10): 1757-1761, 1994.
European Search Report and the European Search Opinion Dated Jul. 17, 2013 From the European Patent Office Re. Application No. 13169606.4.
Communication Pursuant to Rules 70(2) and 70a(2) EPC and Reference to Rule 39(1) EPC Dated Sep. 9, 2013 From the European Patent Office Re. Application No. 13169606.4.

* cited by examiner

*Primary Examiner* — Scott Long
*Assistant Examiner* — Arthur S Leonard

(57) ABSTRACT

Use of an agent which upregulates an activity or amount of miRNA-9 or miRNA-9* is disclosed for the preparation of a medicament for the treatment of a motor neuron disease (MND).

5 Claims, 7 Drawing Sheets
(6 of 7 Drawing Sheet(s) Filed in Color)

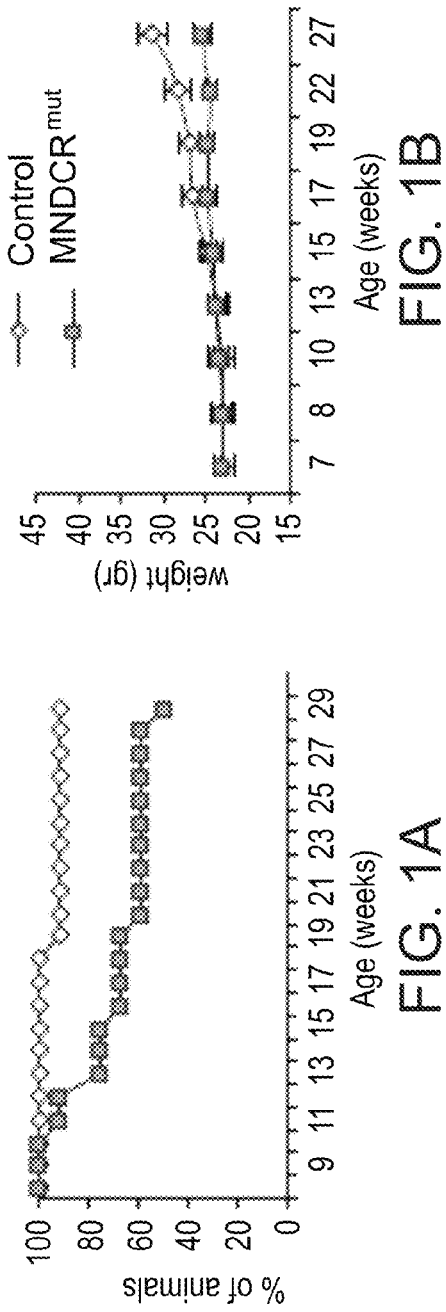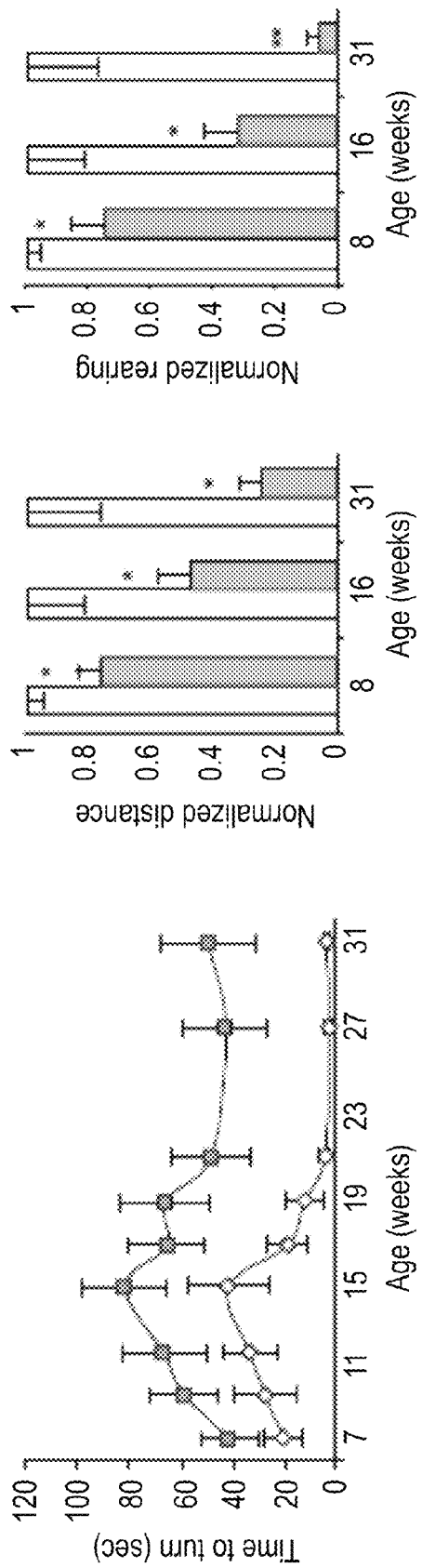

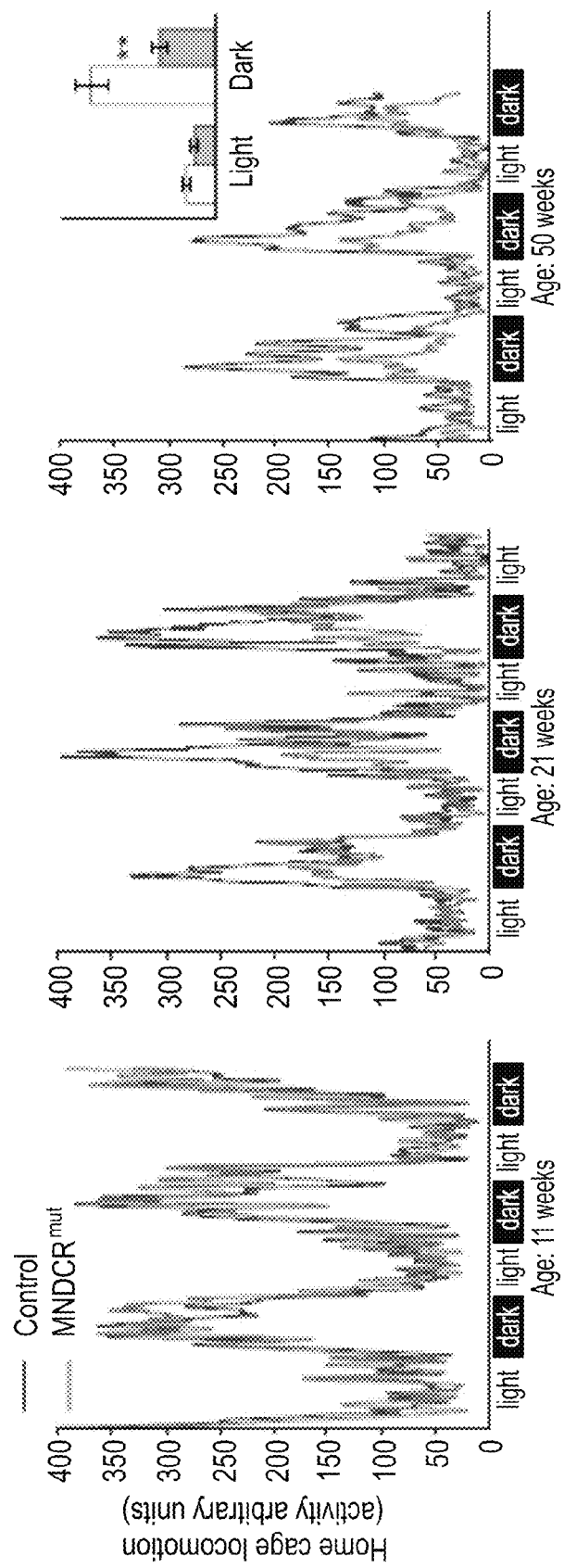

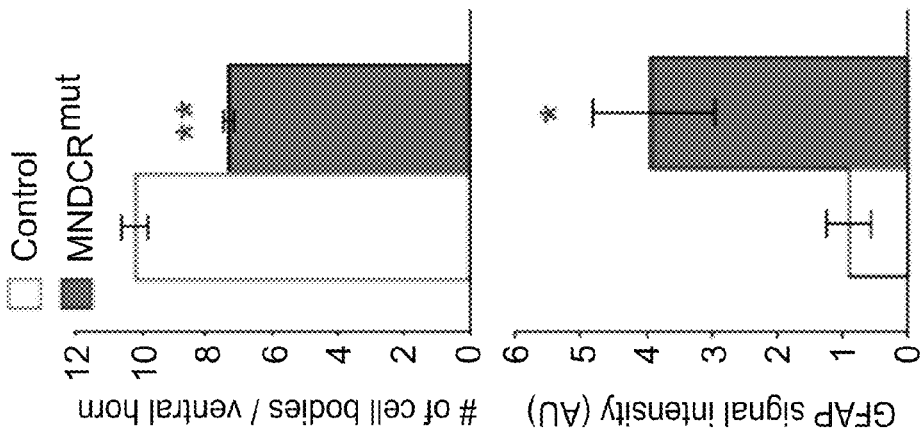
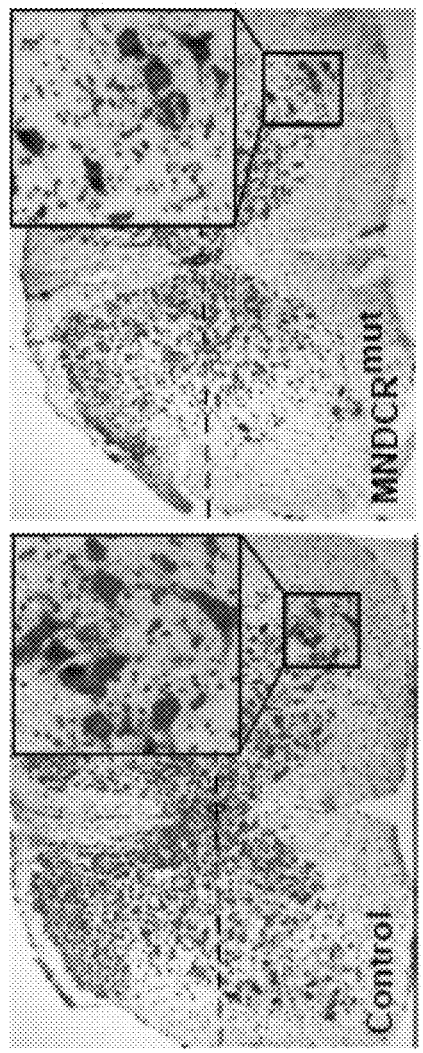
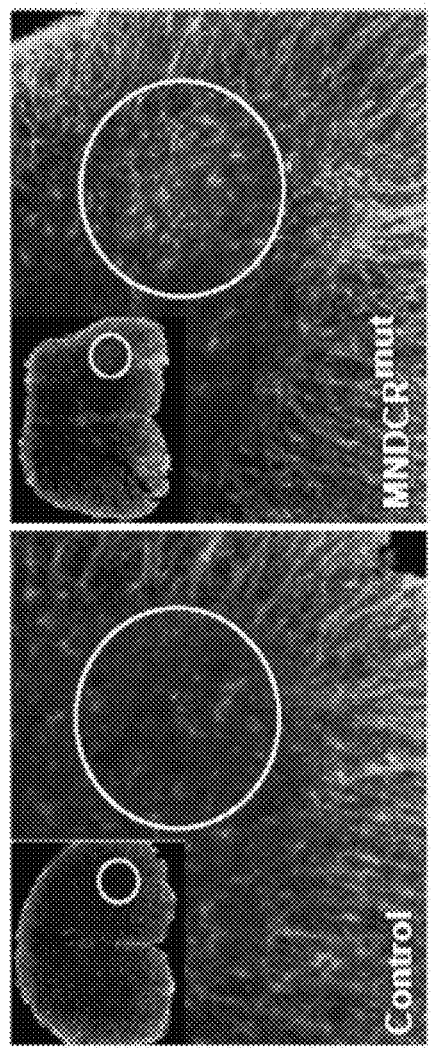

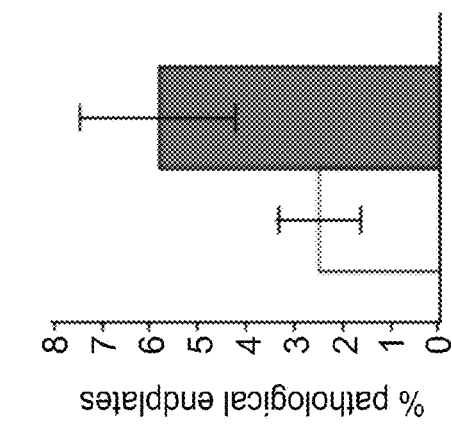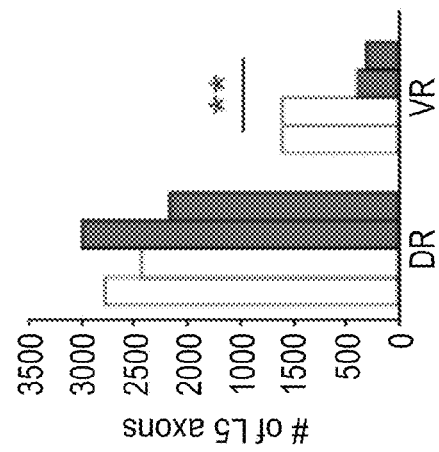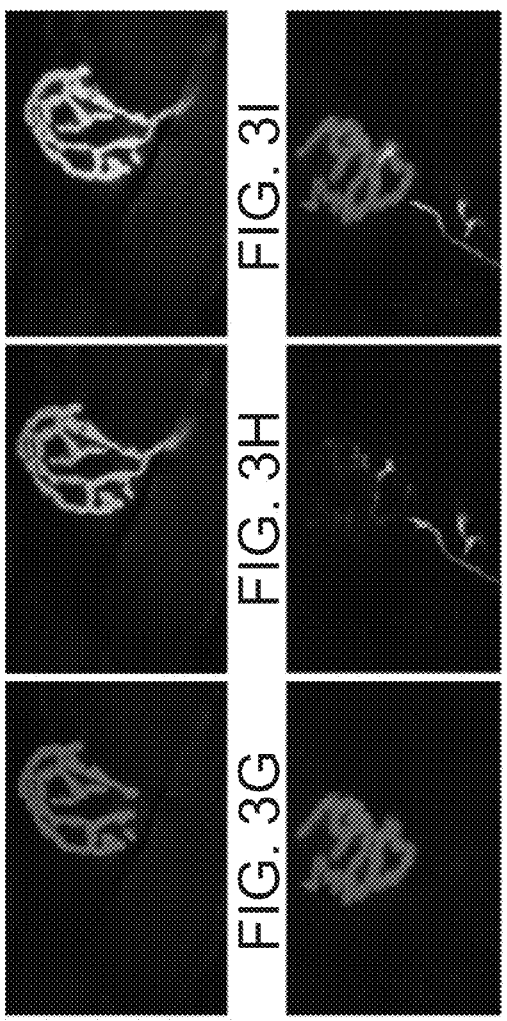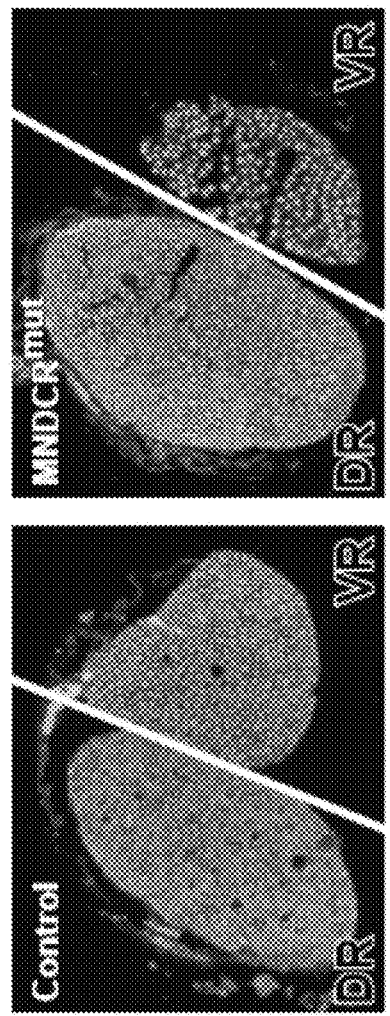

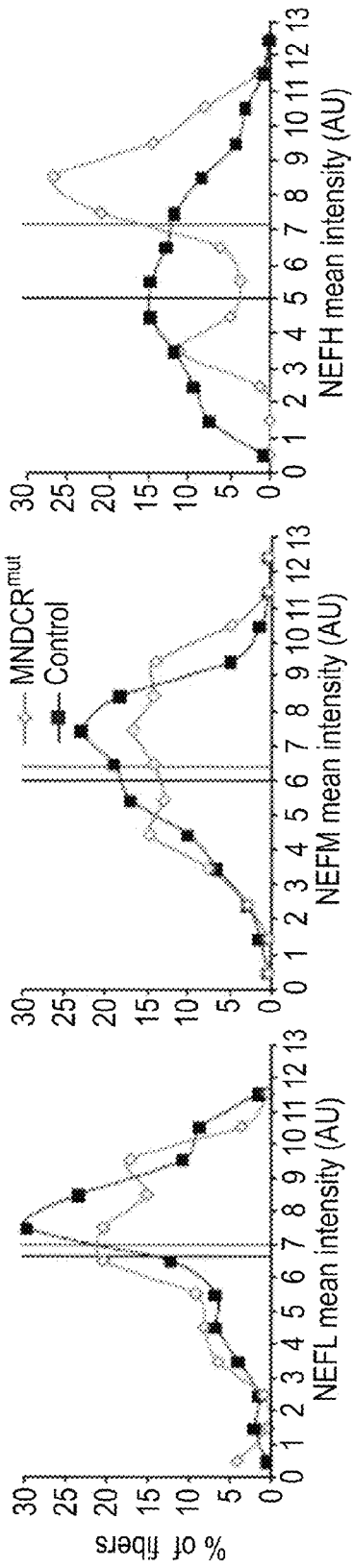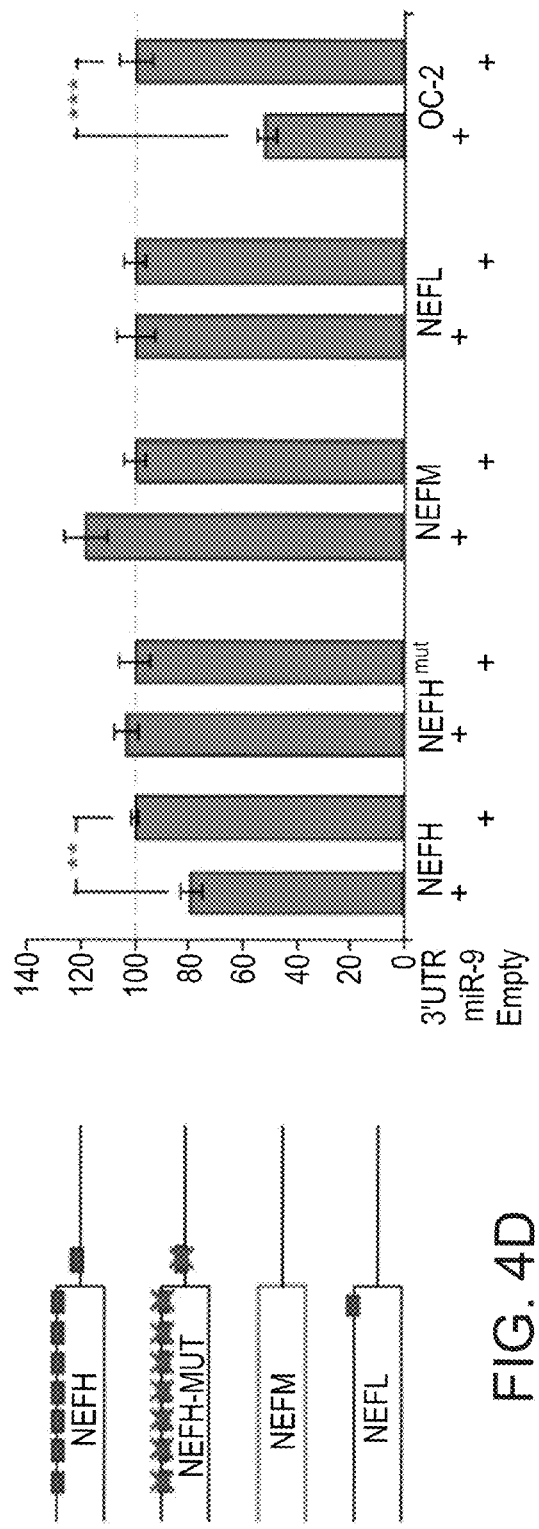
FIG. 4A FIG. 4B FIG. 4C FIG. 4D FIG. 4E

METHODS OF DIAGNOSING AND TREATING MOTOR NEURON DISEASES

RELATED APPLICATIONS

This application is a National Phase of PCT Patent Application No. PCT/IL2009/001148 having International filing date of Dec. 3, 2009, which claims the benefit of priority of U.S. Provisional Patent Application No. 61/193,535 filed on Dec. 5, 2008. The contents of the above applications are all incorporated herein by reference.

FIELD AND BACKGROUND OF THE INVENTION

The present invention, in some embodiments thereof, relates to methods of diagnosing and treating motor neuron diseases and, more particularly, but not exclusively, to Amyotrophic Lateral Sclerosis (ALS).

Motor neuron diseases (MND) belong to a group of neurological disorders attributed to the destruction of motor neurons of the central nervous system and degenerative changes in the motor neuron pathway. Such diseases are different from other neurodegenerative diseases including Parkinson's disease, Alzheimer's disease, olivopontocerebellar atrophy, etc., which are caused by the destruction of neurons other than motor neurons. Typically, MNDs are progressive, degenerative disorders that affect nerves in the upper or lower parts of the body. Generally, MNDs strike in middle age. Symptoms may include difficulty swallowing, limb weakness, slurred speech, impaired gait, facial weakness and muscle cramps. Respiration may be affected in the later stages of these diseases. The cause(s) of most MNDs are not known, but environmental, toxic, viral or genetic factors are all suspects.

Motor neurons, including upper motor neurons and lower motor neurons, affect voluntary muscles, stimulating them to contract. Upper motor neurons originate in the cerebral cortex and send fibers through the brainstem and the spinal cord, and are involved in controlling lower motor neurons. Lower motor neurons are located in the brainstem and the spinal cord and send fibers out to muscles. Lower motor neuron diseases are diseases involving lower motor neuron degeneration. When a lower motor neuron degenerates, the muscle fibers it normally activates become disconnected and do not contract, causing muscle weakness and diminished reflexes. Loss of either type of neurons results in weakness, muscle atrophy (wasting) and painless weakness are the clinical hallmarks of MND.

Amyotrophic Lateral Sclerosis (ALS) is a fatal motor neuron disease characterized by a loss of pyramidal cells in the cerebral motor cortex (i.e., giant Betz cells), anterior spinal motor neurons and brain stem motor neurons, and degeneration thereof into pyramidal cells. ALS shows, from a clinical aspect, both upper motor neurons and lower motor neurons signs, and shows rapid clinical deterioration after onset of the disease, thus leading to death within a few years.

Like many other motor neuron diseases, only a small percentage (about 10%-15%) of ALS is inherited. Genetic epidemiology of ALS has revealed at least six chromosome locations accountable for the inheritance of disease (ALS1 to ALS6). Among these, three genes have been identified. The first was identified in 1993 as the cytosolic Cu/Zn superoxide dismutase (SOD-1) gene that accounts for 20% of the autosomal dominant form of ALS (Rosen et al., 1993, Nature, 1993 Mar. 4; 362(6415):59-62). The discovery of this primary genetic cause of ALS has provided a basis for generating mouse models for this disease. These models are useful for testing therapies that might aid in the treatment of ALS.

The second was named as Alsin, a potential guanine-nucleotide exchange factor (GEF) responsible for the juvenile recessive form of ALS. The third is ALS4 that encodes for a DNA/RNA helicase domain containing protein called Senataxin identified to be linked to the autosomal dominant form of juvenile ALS. Most recently, a mutation in the vesicle associated membrane protein/synaptobrevin associated membrane protein B (VAPB) in a new locus called ALS8, was reported to be associated with an atypical form of ALS.

Riluzole is the sole drug approved for ALS in U.S. and Japan. Riluzole was originally developed as an anticonvulsant inhibiting glutamate release and has been reported in several clinical trials to exhibit only slight efficacy for the survival of ALS patients (Rowland L P and Shneider N A, 2001, N Engl J Med, 344, 1688-1700; and Turner M R and Parton M J, 2001, Semin Neurol 21: 167-175).

Micro-RNAs (also known as miRNAs) are 20- to 24-nucleotide (nt) RNA molecule members of the family of non-coding small RNAs. Micro-RNAs were identified in mammals, worms, fruit flies and plants and are believed to regulate the stability of their target messenger RNA (mRNA) transcripts in a tissue- and cell type-specific manner. Principally, micro-RNAs regulate RNA stability by either binding to the 3'-untranslated region (3'-UTR) of target mRNAs and thereby suppressing translation, or in similar manner to siRNAs, binding to and destroying target transcripts in a sequence-dependent manner.

Micro-RNAs were found to be involved in various cell differentiation pathways. For example, miR-181, was found to be preferentially expressed in the B-lymphoid cells and its ectopic expression in hematopoietic stem/progenitor cells led to an increased fraction of B-lineage cells in vitro and in vivo. In addition, miR-23 was shown to be present in differentiated, but not undifferentiated, human neural progenitor NT2 cells and to regulate a transcriptional repressor in such cells. Other researchers have identified the generation of intron-derived micro-RNA-like molecules (Id-micro-RNA) from these regions as a tool for analysis of gene function and development of gene-specific therapeutics, and predicted possible applications including major gene modulation systems for developmental regulation, intracellular immunity, heterochromatin inactivation, and genomic evolution in eukaryotes (Lin and Ying, 2004b).

Micro-RNAs have been implicated in various neurological diseases such as Fragile X syndrome, spinal muscular atrophy (SMA), early onset parkinsonism (Waisman syndrome) and X-linked mental retaradation (MRX3), as well as various cancers and precancerous conditions such as Wilm's tumor, testicular germ cell tumor, chronic lymphocytic leukemia (CLL), B cell leukemia, precancerous and neoplastic colorectal tissues and Burkkit's lymphoma [reviewed in Gong H, et al., 2004, Mediacl Research Reviews, Published online in Wiley InterScience (www.intersciencedotwileydotcom)].

U.S. Patent Application 20060247193 teaches administration of over 100 miRNAs for the treatment of MNDs including ALS.

U.S. Patent Application 20090246136 teaches administration of miR-206 and/or miR-1 for the treatment of MNDs including ALS.

Figlewicz et al [Human Molecular Genetics, Volume 3, 1994] teaches that variants of the heavy neurofilament subunit are associated with the development of ALS.

Additional relevant background art includes U.S. Patent Application 20080176766.

SUMMARY OF THE INVENTION

According to an aspect of some embodiments of the present invention there is provided a use of an agent which upregulates an activity or amount of miRNA-9 or miRNA-9* for the preparation of a medicament for the treatment of a motor neuron disease (MND).

According to an aspect of some embodiments of the present invention there is provided a use of an agent which upregulates an activity or amount of miRNA-9 or miRNA-9* for the treatment of a motor neuron disease (MND).

According to an aspect of some embodiments of the present invention there is provided a method of diagnosing a MND, the method comprising analyzing an activity or expression of miRNA-9 or miRNA-9* in a sample of a subject in need thereof, wherein a down-regulation of the activity or the expression of the miRNA-9 or miRNA-9* is indicative of the MND.

According to an aspect of some embodiments of the present invention there is provided a method of treating a motor neuron disease (MND), the method comprising administering to a subject in need thereof a therapeutically effective amount of an agent which upregulates an activity or amount of miRNA-9 or miRNA-9*, thereby treating the MND.

According to an aspect of some embodiments of the present invention there is provided a kit for diagnosing a MND comprising an agent which specifically determines a level of miRNA-9 or miRNA-9*.

According to an aspect of some embodiments of the present invention there is provided a transgenic non-human mammal, comprising a cholinergic-specific knock-out of DICER, wherein the mammal exhibits muscular atrophy compared to a wild-type mammal.

According to an aspect of some embodiments of the present invention there is provided a method of identifying an agent for the treatment of a MND, the method comprising administering a candidate agent to the transgenic non-human mammal of the present invention, wherein a decrease in a level of muscular atrophy is indicative of the candidate agent being a therapeutic agent for the treatment of a MND.

According to an aspect of some embodiments of the present invention there is provided a method of identifying an agent for the treatment of a MND, the method comprising:

(a) contacting a motor neuron with a candidate agent;
(b) assessing miR-9 or miR-9* activity or expression in the motor neuron; and
(c) comparing the activity or expression in step (b) with an activity or expression in the absence of the candidate agent, wherein an up-regulation of activity or expression of miR-9 or miR-9* indicates that the candidate compound is a therapeutic agent for the treatment of MND.

According to some embodiments of the invention, the agent is a polynucleotide agent.

According to some embodiments of the invention, the agent comprises a sequence selected from the group consisting of SEQ ID NOs: 1-5.

According to some embodiments of the invention, the MND is selected from the group consisting of Amyotrophic Lateral Sclerosis (ALS), primary lateral sclerosis, progressive muscular atrophy, pseudobulbar palsy, progressive bulbar palsy, lower motor neuron disease and spinal muscular atrophy.

According to some embodiments of the invention, the sample comprises a cerebrospinal fluid (CSF) sample or a blood sample.

According to some embodiments of the invention, the agent comprises a polynucleotide.

According to some embodiments of the invention, the polynucleotide is hybridizable with the miRNA-9 or miRNA-9* under stringent hybridization conditions.

According to some embodiments of the invention, the transgenic non-human mammal is a mouse or a rat.

According to some embodiments of the invention, the knock-out is mediated by Cre-loxP recombination.

According to some embodiments of the invention, the cholinergic specific knock-out is mediated by a cholinergic-specific promoter.

According to some embodiments of the invention, the method further comprises preparing a pharmaceutical composition containing the candidate agent.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying images. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-H are graphs illustrating inferior survival and kinetic activity of the $MNDCR^{mut}$ mice. (A) Survival curve for controls and conditional Dicer knockout mice (control, $MNDCR^{mut}$; n=12,12). (B) Weight-gain of controls and $MNDCR^{mut}$ mice. (C) Time to complete a turn in the pole task for controls and $MNDCR^{mut}$ mice. (D-E) Open field measures at 8, 16 and 31 weeks of age. (D) Ratio of distance traveled in the open-field arena as compared to mean of controls (n=12,12). (E) Ratio of rearing events performed in the open field arena as compared to mean of controls (n=12, 12). (F-H) Homecage locomotion of $MNDCR^{mut}$ and controls, at 11 (F), 21 (G) and 50 (H) weeks of age (n=12,12). Insets: Average of activity throughout the measured period *P<0.05, **P<0.01.

Figure 2A:
Figure 2B:
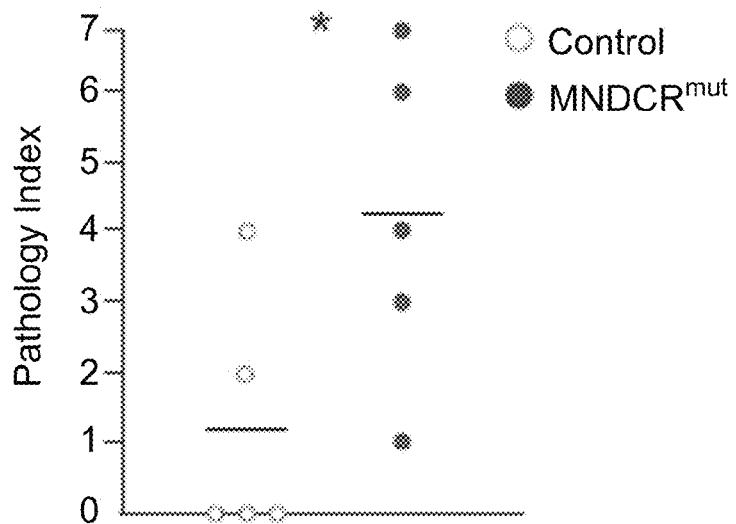
Figure 2C:
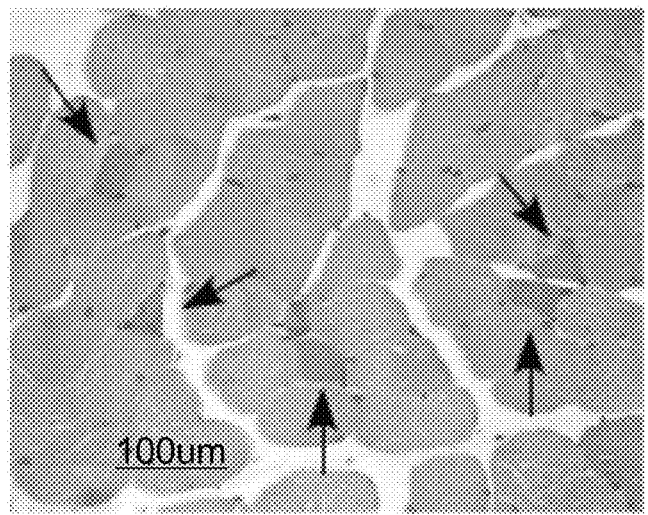

FIGS. 2A-C are graphs and photographs illustrating that $MNDCR^{mut}$ mice exhibit muscular atrophy with signs of denervation. Hindlimb interosseous and gastrocnemius muscle bipolar EMG recording. (A) Representative EMG traces of control (top) and $MNDCR^{mut}$ (bottom) under anesthesia. Frequent fibrillation potentials are annotated by red arrows. (B) For each mouse, EMG findings were graded on a 1-7 scale designated the "EMG Pathology Index", reflecting the intensity and frequency of fibrillation potentials (n=5,5) in coded mice, noting that the electromyographer was blinded as to the genotype of the mouse tested. (C) Hematoxylin and Eosin staining of transverse section through the tibialis MNDCR$^{mut}$ muscle. Angular fibers are marked by arrows. *P<0.05, **P<0.01.

FIGS. 3A-P are photographs and graphs illustrating that MNDCR$^{mut}$ exhibit axonopathy and sclerosis of the spinal cord ventral horns. (A-B) Representative Nissl staining of lumbar sections from a MNDCR$^{mut}$ mouse and a control littermate. Insets are enlargements of a ventral horn area in each section. Dashed line represents the border under which large diameter cells (>20 μm) were counted. (C) Average number of motor neurons counted per ventral horn in lumbar (L2-L3) spinal cord of four months old MNDCR$^{mut}$ mice and controls (12 lumbar sections per animal; n=5,5). (D-E) Representative GFAP immunostained lumber section from four months old MNDCR$^{mut}$ mice and controls. (F) Average signal intensity measured in the latero-ventral horns of lumbar (L2-L3) spinal cord of MNDCR$^{mut}$ mice and controls (arbitrary units, 3 lumbar sections per animal; n=5,5). (G-L) Representative end-plate demonstrating complete overlap (upper) or partial overlap (lower) between the post-synapse (red; rhodamine-labeled bungarotoxin) and pre-synapse (green anti-NEFM antibody) components of the neuromuscular junction. (M) percent of pathological end-plates in MNDCR$^{mut}$ mice and controls (400 synapses/animal; n=2,2). (N-O) Representative dorsal (sensory, left) and ventral (motor, right) roots used for axon number measurements, stained with anti-NEFM antibody. (P) average axon number in dorsal and ventral root of MNDCR$^{mut}$ mice and controls (n=2). *P<0.05, **P<0.01.

FIGS. 4A-G are graphs and diagrams illustrating that mir-9 is specifically downregulated in a model of spinal muscular atrophy and is upstream of coordinated expression of the neurofilament subunits. (A-C) Binned distribution of NF subunit expression intensity. The percentage of axons at any intensity bin is mentioned on the y axis. A-NEFL, B-NEFM, C-NEFH. Black and gray lines represent the global mean intensity of control and MNDCR$^{mut}$ axons, respectively. (D) Illustration of sequences cloned into luciferase reporter constructs used for functional evaluation of miR-9 interactions with NF subunit mRNAs, wherein NEFH$^{mut}$ stands for seed-mutated NEFH. Gray boxes represent miR-9 binding sites (E) Heterologous luciferase reporter assay reveals that miR-9 may function upstream of the NF subunits. Levels of luciferase activity in HEK293 cells transfected with either an empty vector, or a vector over-expressing miR-9. Data is normalized to the activity of a co-transfected beta-galactosidase reporter and presented as percent of luciferase activity in the absence of miR-9. OC-2 (a fragment of the Onecut2 3'UTR) is used as a positive control. (F-G) Wild-type control mouse embryonic stem cells (mESCs) and SMN1$^{mut}$ mESCs, harboring homozygous mSMN1 mutation and two copies of a hSMN2 transgene were differentiated in vitro into motor neurons. The cells were FACS-purified per the expression of GFP transgene, driven by the Hlxb9 promoter. (F)—Volcano plot exemplifying the log 2 ratio of SMN1$^{mut}$/wild-type miRNA expression on the x axis and the log 10 P value obtained by a two-tailed student t-test on the y axis. (G)—qPCR analysis of miR-9 and miR-9* expression in motor neurons derived from SMN1$^{mut}$ mESCs (gray bars) and wild-type mESCs (empty bars) *P<0.05, **P<0.01.

DESCRIPTION OF SPECIFIC EMBODIMENTS OF THE INVENTION

The present invention, in some embodiments thereof, relates to methods of diagnosing and treating motor neuron diseases and, more particularly, but not exclusively, to Amyotrophic Lateral Sclerosis (ALS).

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

It is known that miRNA plays a crucial role in post-transcriptional gene regulation in morphological and functional plasticity of post-mitotic vertebrate neurons. Further, alterations in the function of miRNA contribute to the susceptibility to neurodegenerative disease.

The present inventors have generated a transgenic mouse that selectively lacks microRNA activity in post-mitotic motor neurons (MNs). The mouse exhibits hallmarks of MND (motor neuron disease), including sclerosis of the spinal cord ventral horns, aberrant end-plate architecture and muscular atrophy with signs of denervation (FIGS. 2A-C and 3A-P).

Using this model, the present inventors found that neurofilament heavy subunit (NFH) expression is up-regulated in miRNA-deficient MNs (FIGS. 4A-C).

Figure 4G:
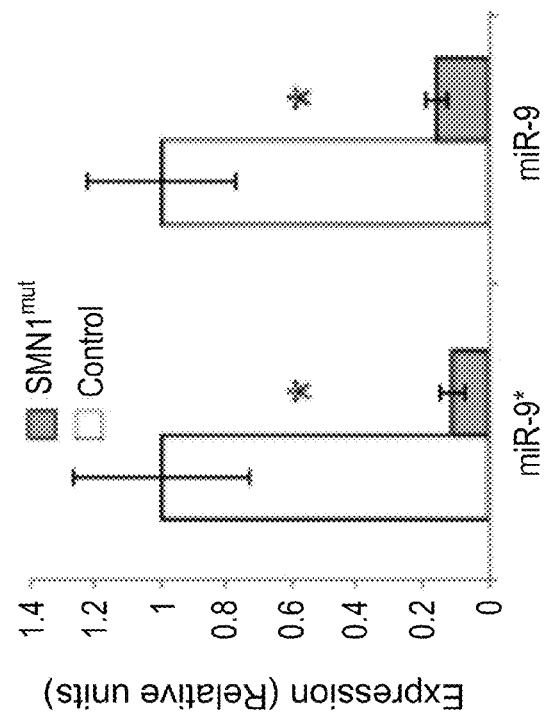
Figure 4F:
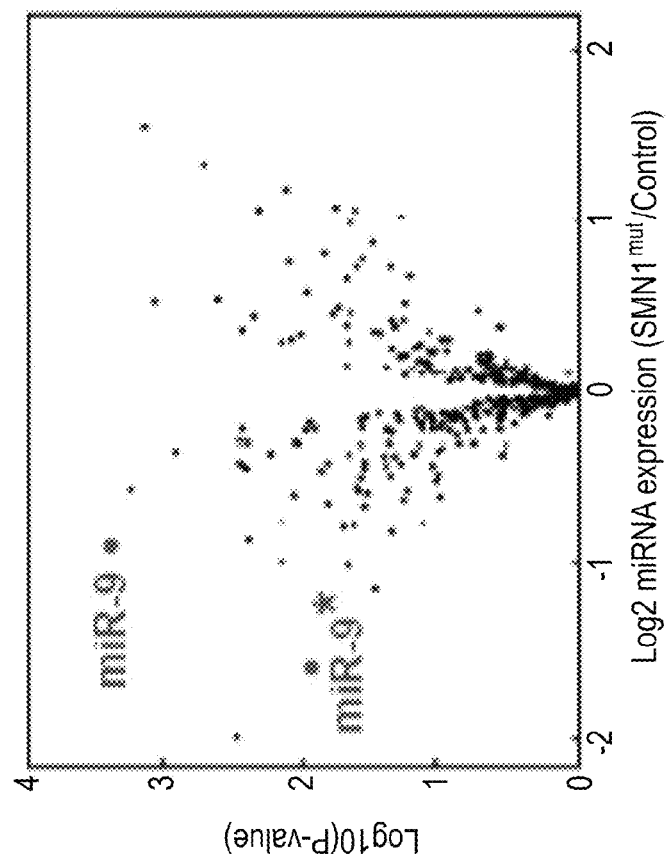

The present inventors showed that miR-9 is specifically down-regulated in a different mouse model of spinal muscular atrophy (FIGS. 4F-G).

Finally, the present inventors showed that NFH is a target for regulation by miR-9 (FIG. 4E).

The present inventors conclude from these findings that miR-9 may be involved in MNDs and as such the present inventors propose that miR-9 may serve as a potential target both for treatments and diagnoses of MNDs.

Thus, according to one aspect of the present invention, there is provided a method of diagnosing a motor neuron disease (MND), the method comprising analyzing an activity or expression of miRNA-9 or miRNA-9* in a sample of a subject in need thereof, wherein a down-regulation of the activity or expression of miRNA-9 or miRNA-9* is indicative of the MND.

As used herein, the term "diagnosing" refers to classifying a pathology (e.g., a disease, disorder, syndrome, medical condition and/or a symptom thereof), determining a severity of the pathology, monitoring the progression of a pathology, forecasting an outcome of the pathology and/or prospects of recovery (e.g., prognosis).

The phrase "motor neuron disease (MND)" as used herein, refers to a neurological disorder that selectively destroys motor neurons. As such, diseases such as Huntington's chorea are not classified as MNDs.

Examples of motor neuron diseases include, but are not limited to Amyotrophic Lateral Sclerosis (ALS), also known as Lou Gehrig's Disease, primary lateral sclerosis, progressive muscular atrophy, pseudobulbar palsy, progressive bulbar palsy, lower motor neuron disease and spinal muscular atrophy 1 (SMA1, Werdnig-Hoffmann Disease), Spinal Muscular Atrophy Type 2 (SMA2) and Spinal Muscular Atrophy Type 3 (SMA3, Kugelberg-Welander Disease) and Charcot-Marie-Tooth Disorders.

As used herein "a biological sample" refers to a sample of fluid or tissue sample derived from a subject. Examples of fluid samples include, but are not limited to, blood, plasma, serum, spinal fluid, lymph fluid, tears, saliva, sputum and milk. An example of a tissue sample includes a brain tissue sample or a nerve tissue sample (e.g. for post-mortum diagnosis).

Methods of obtaining such biological samples are known in the art including but not limited to standard blood retrieval procedures and lumbar puncture.

As used herein, the term "subject" refers to an animal, preferably a mammal, most preferably a human being. The subject may be healthy or showing preliminary signs of a MND, such as muscle fatigue. Alternatively, the subject may have a genetic predisposition to the disease.

Detection of the level of the miRNA-9 or 9* can be effected using various methods known in the art, including RNA-based hybridization methods (e.g., Northern blot hybridization, RNA in situ hybridization and chip hybridization) and reverse transcription-based detection methods (e.g., RT-PCR, quantitative RT-PCR, semi-quantitative RT-PCR, real-time RT-PCR, in situ RT-PCR, primer extension, mass spectroscopy, sequencing, sequencing by hybridization, LCR (LAR), Self-Sustained Synthetic Reaction (3SR/NASBA), Q-Beta (Qb) Replicase reaction, cycling probe reaction (CPR), a branched DNA analysis, and detection of at least one nucleic acid change).

Total cellular RNA can be isolated from a biological sample using any suitable technique such as the single-step guanidinium-thiocyanate-phenol-chloroform method described in Chomczynski and Sacchi, Anal. Biochem. 162: 156-159 (1987) or by using kits such as the Tri-Reagent kit (Sigma).

Following is a non-limiting list of RNA-based hybridization methods which can be used to detect the miRNA of the present invention.

Northern Blot analysis—This method involves the detection of a particular RNA in a mixture of RNAs. An RNA sample is denatured by treatment with an agent (e.g., formaldehyde) that prevents hydrogen bonding between base pairs, ensuring that all the RNA molecules have an unfolded, linear conformation. The individual RNA molecules are then separated according to size by gel electrophoresis and transferred to a nitrocellulose or a nylon-based membrane to which the denatured RNAs adhere. The membrane is then exposed to labeled DNA, RNA or oligonucleotide (composed of deoxyribo or ribonucleotides) probes. Probes may be labeled using radio-isotopes or enzyme linked nucleotides. Detection may be using autoradiography, colorimetric reaction or chemiluminescence. This method allows both quantitation of an amount of particular RNA molecules and determination of its identity by a relative position on the membrane which is indicative of a migration distance in the gel during electrophoresis.

RNA in situ hybridization stain—In this method DNA, RNA or oligonucleotide (composed of deoxyribo or ribonucleotides) probes are attached to the RNA molecules present in the cells. Generally, the cells are first fixed to microscopic slides to preserve the cellular structure and to prevent the RNA molecules from being degraded and then are subjected to hybridization buffer containing the labeled probe. The hybridization buffer includes reagents such as formamide and salts (e.g., sodium chloride and sodium citrate) which enable specific hybridization of the DNA or RNA probes with their target mRNA molecules in situ while avoiding non-specific binding of probe. Those of skills in the art are capable of adjusting the hybridization conditions (i.e., temperature, concentration of salts and formamide and the like) to specific probes and types of cells. Following hybridization, any unbound probe is washed off and the slide is subjected to either a photographic emulsion which reveals signals generated using radio-labeled probes or to a colorimetric reaction which reveals signals generated using enzyme-linked labeled probes.

Hybridization to oligonucleotide arrays—The chip/array technology has already been applied with success in numerous cases. For example, the screening of mutations has been undertaken in the BRCA1 gene, in S. cerevisiae mutant strains, and in the protease gene of HW-1 virus [see Hacia et al., (1996) Nat Genet 1996; 14(4):441-447; Shoemaker et al., (1996) Nat Genet 1996; 14(4):450-456; Kozal et al., (1996) Nat Med 1996; 2(7):753-759].

The nucleic acid sample which includes the candidate region to be analyzed is isolated, amplified and labeled with a reporter group. This reporter group can be a fluorescent group such as phycoerythrin. The labeled nucleic acid is then incubated with the probes immobilized on the chip using a fluidics station. For example, Manz et al. (1993) Adv in Chromatogr 1993; 33:1-66 describe the fabrication of fluidics devices and particularly microcapillary devices, in silicon and glass substrates.

Once the reaction is completed, the chip is inserted into a scanner and patterns of hybridization are detected. The hybridization data is collected, as a signal emitted from the reporter groups already incorporated into the nucleic acid, which is now bound to the probes attached to the chip. Probes that perfectly match a sequence of the nucleic acid sample generally produce stronger signals than those that have mismatches. Since the sequence and position of each probe immobilized on the chip is known, the identity of the nucleic acid hybridized to a given probe can be determined.

Preferably, the oligonucleotide probes utilized by the various hybridization techniques described hereinabove are capable of hybridizing to miRNA 9 or 9* under stringent hybridization conditions.

By way of example, hybridization of short nucleic acids (below 200 bp in length, e.g. 17-40 bp in length) can be effected by the following hybridization protocols depending on the desired stringency; (i) hybridization solution of 6×SSC and 1% SDS or 3 M TMACl, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature of 1-1.5° C. below the Tm, final wash solution of 3 M TMACl, 0.01 M sodium phosphate (pH 6.8), 1 mM EDTA (pH 7.6), 0.5% SDS at 1-1.5° C. below the Tm (stringent hybridization conditions) (ii) hybridization solution of 6×SSC and 0.1% SDS or 3 M TMACl, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature of 2-2.5° C. below the Tm, final wash solution of 3 M TMACl, 0.01 M sodium phosphate (pH 6.8), 1 mM EDTA (pH 7.6), 0.5% SDS at 1-1.5° C. below the Tm, final wash solution of 6×SSC, and final wash at 22° C. (stringent to moderate hybridization conditions); and (iii) hybridization solution of 6×SSC and 1% SDS or 3 M TMACl, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature at 2.5-3° C. below the Tm and final wash solution of 6×SSC at 22° C. (moderate hybridization solution).

For example, a micro-RNA molecule having a nucleic acid sequence as set forth in SEQ ID NO:1 can be detected using an oligonucleotide probe having a nucleic acid sequence as set forth in SEQ ID NO:3. For example, a micro-RNA molecule having a nucleic acid sequence as set forth in SEQ ID NO:2 can be detected using an oligonucleotide probe having a nucleic acid sequence as set forth in SEQ ID NO:4.

As is mentioned before, miRNA-9 or 9* can be also detected using a reverse-transcription based method. Reverse-transcription utilizes RNA template, primers (specific or random), reverse transcriptase (e.g., MMLV-RT) and deoxyribonucleotides to form (i.e., synthesize) a complementary DNA (cDNA) molecule based on the RNA template sequence. Once synthesized, the single strand cDNA molecule or the double strand cDNA molecule (which is synthesized based on the single strand cDNA) can be used in various DNA based detection methods such as RT-PCR analysis.

RT-PCR analysis—This method uses PCR amplification of relatively rare RNA molecules. First, RNA molecules are purified from cells and converted into complementary DNA (cDNA) using a reverse transcriptase enzyme (such as an MMLV-RT) and primers such as oligo-dT, random hexamers, or gene-specific primers. Then by applying gene-specific primers and Taq DNA polymerase, a PCR amplification reaction is carried out in a PCR machine. Those of ordinary skill in the art are capable of selecting the length and sequence of the gene-specific primers and the PCR conditions (i.e., annealing temperatures, number of cycles, and the like) that are suitable for detecting specific RNA molecules. It will be appreciated that a semi-quantitative RT-PCR reaction can be employed, by adjusting the number of PCR cycles and comparing the amplification product to known controls.

In situ RT-PCR stain—This method is described by: Nuovo, G. J. et al. (1993). Intracellular localization of polymerase chain reaction (PCR)-amplified hepatitis C cDNA. Am J Surg Pathol 17, 683-690); and Komminoth, P. et al. (1994) Evaluation of methods for hepatitis C virus detection in archival liver biopsies. Comparison of histology, immunohistochemistry, in situ hybridization, reverse transcriptase polymerase chain reaction (RT-PCR) and in situ RT-PCR. Pathol Res Pract 190, 1017-1025). Briefly, the RT-PCR reaction on fixed cells involves the incorporation of labeled nucleotides in the reaction. The reaction is effected using a specific in situ RT-PCR apparatus, such as the laser-capture microdissection PixCell II™ Laser Capture Microdissection (LCM) system available from Arcturus Engineering (Mountainview, Calif., USA).

The probes and primers (i.e. detecting agents) that are used to specifically determine a level of miRNA-9 or miRNA-9* may be packaged in a kit and labeled for the use of diagnosing a motor neuron disease. The kits comprising primers may further include a DNA polymerase enzyme, such as a thermostable DNA polymerase, a reverse transcriptase enzyme, a mixture of dNTPs, a concentrated polymerase chain reaction buffer and a concentrated reverse transcription buffer. The detecting agents can include nucleotide analogs and/or a labeling moiety, e.g., directly detectable moiety such as a fluorophore (fluorochrome) or a radioactive isotope, or indirectly detectable moiety, such as a member of a binding pair, such as biotin, or an enzyme capable of catalyzing a non-soluble colorimetric or luminometric reaction. The kit may also comprise at least one precast gel for executing RT-PCR. In addition, the kit may further include at least one container containing reagents for detection of electrophoresed nucleic acids. Such reagents include those which directly detect nucleic acids, such as fluorescent intercalating agent or silver staining reagents, or those reagents directed at detecting labeled nucleic acids, such as, but not limited to, ECL reagents. The kit preferably includes a notice associated therewith in a form prescribed by a governmental agency regulating the manufacture, use or sale of diagnostic kits. Detailed instructions for use, storage and trouble shooting may also be provided with the kit.

As mentioned, MND diagnosis may also be effected by analyzing an activity of miRNA-9 or miRNA-9*.

Since miRNAs are polynucleotides that bind to target transcripts in a sequence-specific manner, causing the destruction thereof, it is possible to analyze an activity of miRNA-9 or miRNA-9* by analyzing an expression of at least one of its target transcripts. A down-regulation of activity of miRNA-9 should inevitably lead to an up-regulation in expression of its target transcript.

Methods of ascertaining targets for miRNA-9 or miRNA-9* are known in the art. For example various bioinformatic tools are available for analyzing gene sequences and determining if they comprise a miRNA binding sites (i.e. targets). Exemplary tools include, but are not limited to TargetScan [Lewis B P, Burge C B, Bartel D P (2005) Cell 120: 15-20; Lewis B P, Shih I H, Jones-Rhoades M W, Bartel D P, Burge C B (2003) Cell 115: 787-798] (http://wwwdottargetscandotorg) and PicTar [Krek A, Grun D, Poy M N, Wolf R, Rosenberg L, et al. (2005) Nat Genet 37: 495-500] (http://genomedotucscdotedu).

In order to ensure that false positive assignments of miRs to targets does not occur, targets may be selected based on evolutionary conservation in at least two species (e.g. human and mouse) or more.

Other methods may be used to increase the accuracy of results obtained using bioinformatic methods e.g. a noise tolerance analysis.

According to one embodiment, the target transcript analyzed is not neurofilament heavy subunit (NFH).

It will be appreciated that analyzing an expression of the target transcript may be effected on the RNA or the protein level.

Expression levels of proteins can be determined using methods known in the arts.

Enzyme linked immunosorbent assay (ELISA): This method involves fixation of a sample (e.g., fixed cells or a proteinaceous solution) containing a protein substrate to a surface such as a well of a microtiter plate. A substrate specific antibody coupled to an enzyme is applied and allowed to bind to the substrate. Presence of the antibody is then detected and quantitated by a colorimetric reaction employing the enzyme coupled to the antibody. Enzymes commonly employed in this method include horseradish peroxidase and alkaline phosphatase. If well calibrated and within the linear range of response, the amount of substrate present in the sample is proportional to the amount of color produced. A substrate standard is generally employed to improve quantitative accuracy.

Western blot: This method involves separation of a substrate from other protein by means of an acrylamide gel followed by transfer of the substrate to a membrane (e.g., nylon or PVDF). Presence of the substrate is then detected by antibodies specific to the substrate, which are in turn detected by antibody binding reagents. Antibody binding reagents may be, for example, protein A, or other antibodies. Antibody binding reagents may be radiolabeled or enzyme linked as described hereinabove. Detection may be by autoradiography, colorimetric reaction or chemiluminescence. This method allows both quantitation of an amount of substrate and determination of its identity by a relative position on the membrane which is indicative of a migration distance in the acrylamide gel during electrophoresis.

Radio-immunoassay (RIA): In one version, this method involves precipitation of the desired protein (i.e., the substrate) with a specific antibody and radiolabeled antibody binding protein (e.g., protein A labeled with $I^{125}$) immobilized on a precipitable carrier such as agarose beads. The number of counts in the precipitated pellet is proportional to the amount of substrate.

In an alternate version of the RIA, a labeled substrate and an unlabelled antibody binding protein are employed. A sample containing an unknown amount of substrate is added in varying amounts. The decrease in precipitated counts from the labeled substrate is proportional to the amount of substrate in the added sample.

Fluorescence activated cell sorting (FACS): This method involves detection of a substrate in situ in cells by substrate specific antibodies. The substrate specific antibodies are linked to fluorophores. Detection is by means of a cell sorting machine which reads the wavelength of light emitted from each cell as it passes through a light beam. This method may employ two or more antibodies simultaneously.

Immunohistochemical analysis: This method involves detection of a substrate in situ in fixed cells by substrate specific antibodies. The substrate specific antibodies may be enzyme linked or linked to fluorophores. Detection is by microscopy and subjective or automatic evaluation. If enzyme linked antibodies are employed, a colorimetric reaction may be required. It will be appreciated that immunohistochemistry is often followed by counterstaining of the cell nuclei using for example Hematoxyline or Giemsa stain.

In situ activity assay: According to this method, a chromogenic substrate is applied on the cells containing an active enzyme and the enzyme catalyzes a reaction in which the substrate is decomposed to produce a chromogenic product visible by a light or a fluorescent microscope.

In vitro activity assays: In these methods the activity of a particular enzyme is measured in a protein mixture extracted from the cells. The activity can be measured in a spectrophotometer well using colorimetric methods or can be measured in a non-denaturing acrylamide gel (i.e., activity gel). Following electrophoresis the gel is soaked in a solution containing a substrate and colorimetric reagents. The resulting stained band corresponds to the enzymatic activity of the protein of interest. If well calibrated and within the linear range of response, the amount of enzyme present in the sample is proportional to the amount of color produced. An enzyme standard is generally employed to improve quantitative accuracy.

As mentioned, a diagnosis for an MND may be considered positive when there is a down-regulation of miRNA-9 or miRNA-9*.

Typically, the level of miRNA-9 or miRNA-9* in the patients sample is compared to that of at least one healthy individual (i.e. a control free of MND). A down-regulation by at least 1.5 fold is indicative of an MND. According to another embodiment, a down-regulation by at least 2 fold is indicative of an MND. Preferably, the control sample is of the identical biological fluid and comes from a healthy subject of the same species, age, gender and from the same sub-population (e.g. smoker/nonsmoker). Alternatively, control data may be taken from databases and literature. It will be appreciated that the control sample may also be taken from the diseased subject at a particular time-point, in order to analyze the progression of the disease.

Following analysis of activity and/or expression of miRNA-9 or miRNA-9*, the results are typically recorded and the subject is informed. The diagnosis may be substantiated with other means including those that make up the El Escorial criteria. Other diagnostic methods that can be used in conjunction with the method of the present invention are those that involve transcranial magnetic stimulation (TMS). This noninvasive procedure creates a magnetic pulse inside the brain that stimulates motor activity in a certain area of the body. Electrodes taped to different areas of the body pick up and record the electrical activity in the muscles.

It will be appreciated that the diagnostic method of the present invention may also be substantiated with other tests to rule out the involvement of other diseases or to measure the extent of muscle involvement. Below is a list of such tests:

1. Electromyography (EMG) is used to diagnose muscle and nerve dysfunction and spinal cord disease. It is also used to measure the speed at which impulses travel along a particular nerve. EMG records the electrical activity from the brain and/or spinal cord to a peripheral nerve root (found in the arms and legs) that controls muscles during contraction and at rest. Very fine wire electrodes are inserted one at a time into a muscle to assess changes in electrical voltage that occur during movement and when the muscle is at rest. The electrodes are attached to a recording instrument. Testing usually lasts about an hour or more, depending on the number of muscles and nerves to be tested.

2. EMG is usually done in conjunction with a nerve conduction velocity study. This procedure also measures electrical energy to test the nerve's ability to send a signal. A technician tapes two sets of flat electrodes on the skin over the muscles. The first set of electrodes is used to send small pulses of electricity (similar to a jolt from static electricity) to stimulate the nerve that directs a particular muscle. The second set of electrodes transmits the responding electrical signal to a recording machine. The physician then reviews the response to verify any nerve damage or muscle disease.

2. Laboratory screening tests of blood, urine, or other substances can rule out muscle diseases and other disorders that may have symptoms similar to those of MND. For example, analysis of the fluid that surrounds the brain and spinal cord can detect a number of disorders, including PPS. Blood tests may be ordered to measure levels of the protein creatine kinase (which is needed for the chemical reactions that produce energy for muscle contractions); high levels may help diagnose muscle diseases such as muscular dystrophy.

3. Magnetic resonance imaging (MRI) uses computer-generated radio waves and a powerful magnetic field to produce detailed images of body structures including tissues, organs, bones, and nerves. These images can help diagnose brain and spinal cord tumors, eye disease, inflammation, infection, and vascular irregularities that may lead to stroke. MRI can also detect and monitor degenerative disorders such as multiple sclerosis and can document brain injury from trauma. MRI is often used to rule out diseases other than the MNDs that affect the head, neck, and spinal cord.

4. Muscle or nerve biopsy can help confirm nerve disease and nerve regeneration. A small sample of the muscle or nerve is removed under local anesthetic and studied under a microscope. The sample may be removed either surgically, through a slit made in the skin, or by needle biopsy, in which a thin hollow needle is inserted through the skin and into the muscle. A small piece of muscle remains in the hollow needle when it is removed from the body. Although this test can provide valuable information about the degree of damage, it is an invasive procedure that may itself cause neuropathic side effects. Many experts do not believe that a biopsy is always needed for diagnosis.

Since the present inventors showed that miRNA-9 and 9* are down-regulated in MND mouse models, the present inventors also propose that these miRNAs can be used to treat such diseases.

Thus, according to another aspect of the present invention, there is provided a method of treating a motor neuron disease (MND), the method comprising administering to a subject in need thereof a therapeutically effective amount of an agent which upregulates an activity or amount of miRNA-9 or miRNA-9*, thereby treating the MND.

Agents of the present invention which upregulate an activity or amount of miRNA-9 or miRNA-9* include, but are not limited to, chemicals, antibiotic compounds known to modify gene expression, modified or unmodified polynucleotides (including oligonucleotides), polypeptides, peptides, small RNA molecules and miRNAs.

Micro-RNAs are processed from pre-miR (pre-micro-RNA precursors). Pre-miRs are a set of precursor miRNA molecules transcribed by RNA polymerase III that are efficiently processed into functional miRNAs, e.g., upon transfection into cultured cells. Accordingly, a pre-miR can be used to elicit specific miRNA activity in cell types that do not normally express this miRNA, thus addressing the function of its target by down regulating its expression in a "gain of (miRNA) function" experiment. Pre-miR designs exist to all of the known miRNAs listed in the miRNA Registry and can be readily designed for any research.

Thus, according to preferred embodiments of the present invention, upregulating the function and/or activity of the miRNAs of the present invention is effected using a polynucleotide which comprises at least 25 consecutive nucleotides of the nucleic acid sequence set forth in SEQ ID NOs: 5, 6 or 7, more preferably, at least 30, more preferably, at least 35, more preferably, at least 40, more preferably, at least 45, more preferably, at least 50, more preferably, at least 55, more preferably, at least 60, more preferably, at least 65, more preferably, at least 70, more preferably, at least 75, more preferably, at least 80, more preferably, at least 85 consecutive nucleotides of the nucleic acid sequence set forth in SEQ NO:5, 6 or 7.

Naturally occurring pre-miRNAs are generated from longer primary transcripts (pri-miRNAs—accession number at the miRbase=MI0000466; MI0000467; MI0000468) by a ribonuclease, e.g., Drosha.

As used herein, the term "pri-miRNA" refers to RNA precursors of pre-miRNAs, e.g., RNA precursors which contain miRNAs and are cleaved by Drosha. Accordingly, the present invention also contemplates upregulating a function and/or activity of miRNA-9 or miRNA-9* by administration of the pri-miRNA-9.

Alternatively, agents capable of upregulating miRNA function and/or activity may be the miRNAs themselves—i.e. miRNA 9 and/or 9*.

Thus, according to preferred embodiments of the present invention, upregulating the function of the miRNAs of the present invention is effected using a polynucleotide which comprises at least 21 consecutive nucleotides of the nucleic acid sequence set forth in SEQ ID NOs:1 or 3, more preferably, at least 22, more preferably, at least 23 consecutive nucleotides of the nucleic acid sequence set forth in SEQ NOs:1 or 3.

The term "polynucleotide" refers to a single-stranded or double-stranded oligomer or polymer of ribonucleic acid (RNA), deoxyribonucleic acid (DNA) or mimetics thereof. This term includes polynucleotides and/or oligonucleotides derived from naturally occurring nucleic acids molecules (e.g., RNA or DNA), synthetic polynucleotide and/or oligonucleotide molecules composed of naturally occurring bases, sugars, and covalent internucleoside linkages (e.g., backbone), as well as synthetic polynucleotides and/or oligonucleotides having non-naturally occurring portions, which function similarly to respective naturally occurring portions.

The polynucleotides (including oligonucleotides) designed according to the teachings of the present invention can be generated according to any oligonucleotide synthesis method known in the art, including both enzymatic syntheses or solid-phase syntheses. Equipment and reagents for executing solid-phase synthesis are commercially available from, for example, Applied Biosystems. Any other means for such synthesis may also be employed; the actual synthesis of the oligonucleotides is well within the capabilities of one skilled in the art and can be accomplished via established methodologies as detailed in, for example: Sambrook, J. and Russell, D. W. (2001), "Molecular Cloning: A Laboratory Manual"; Ausubel, R. M. et al., eds. (1994, 1989), "Current Protocols in Molecular Biology," Volumes I-III, John Wiley & Sons, Baltimore, Md.; Perbal, B. (1988), "A Practical Guide to Molecular Cloning," John Wiley & Sons, New York; and Gait, M. J., ed. (1984), "Oligonucleotide Synthesis"; utilizing solid-phase chemistry, e.g. cyanoethyl phosphoramidite followed by deprotection, desalting, and purification by, for example, an automated trityl-on method or HPLC.

The polynucleotide of the present invention may be modified using various methods known in the art. However, measures are taken to ensure that the miR function is maintained.

For example, the oligonucleotides or polynucleotides of the present invention may comprise heterocylic nucleosides consisting of purines and the pyrimidines bases, bonded in a 3'-to-5' phosphodiester linkage.

Preferably used oligonucleotides or polynucleotides are those modified either in backbone, internucleoside linkages, or bases, as is broadly described hereinunder.

Specific examples of preferred oligonucleotides or polynucleotides useful according to this aspect of the present invention include oligonucleotides or polynucleotides containing modified backbones or non-natural internucleoside linkages. Oligonucleotides or polynucleotides having modified backbones include those that retain a phosphorus atom in the backbone, as disclosed in U.S. Pat. Nos. 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Preferred modified oligonucleotide or polynucleotide backbones include, for example: phosphorothioates; chiral phosphorothioates; phosphorodithioates; phosphotriesters; aminoalkyl phosphotriesters; methyl and other alkyl phosphonates, including 3'-alkylene phosphonates and chiral phosphonates; phosphinates; phosphoramidates, including 3'-amino phosphoramidate and aminoalkylphosphoramidates; thionophosphoramidates; thionoalkylphosphonates; thionoalkylphosphotriesters; and boranophosphates having normal 3'-5' linkages, 2'-5' linked analogues of these, and those having inverted polarity wherein the adjacent pairs of nucleoside units are linked 3'-5' to 5'-3' or 2'-5' to 5'-2'. Various salts, mixed salts, and free acid forms of the above modifications can also be used.

Alternatively, modified oligonucleotide or polynucleotide backbones that do not include a phosphorus atom therein have backbones that are formed by short-chain alkyl or cycloalkyl internucleoside linkages, mixed heteroatom and alkyl or cycloalkyl internucleoside linkages, or one or more short-chain heteroatomic or heterocyclic internucleoside linkages. These include those having morpholino linkages (formed in part from the sugar portion of a nucleoside); siloxane backbones; sulfide, sulfoxide, and sulfone backbones; formacetyl and thioformacetyl backbones; methylene formacetyl and thioformacetyl backbones; alkene-containing backbones; sulfamate backbones; methyleneimino and methylenehydrazino backbones; sulfonate and sulfonamide backbones; amide backbones; and others having mixed N, O, S and $CH_2$ component parts, as disclosed in U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086;

5,602,240; 5,610,289; 5,602,240; 5,608,046; 5,610,289; 5,618,704; 5,623,070; 5,663,312; 5,633,360; 5,677,437; and 5,677,439.

Other oligonucleotides or polynucleotides which may be used according to the present invention are those modified in both sugar and the internucleoside linkage, i.e., the backbone of the nucleotide units is replaced with novel groups. The base units are maintained for complementation with the appropriate polynucleotide target. An example of such an oligonucleotide mimetic includes a peptide nucleic acid (PNA). A PNA oligonucleotide refers to an oligonucleotide where the sugar-backbone is replaced with an amide-containing backbone, in particular an aminoethylglycine backbone. The bases are retained and are bound directly or indirectly to aza-nitrogen atoms of the amide portion of the backbone. United States patents that teach the preparation of PNA compounds include, but are not limited to, U.S. Pat. Nos. 5,539,082; 5,714,331; and 5,719,262; each of which is herein incorporated by reference. Other backbone modifications which may be used in the present invention are disclosed in U.S. Pat. No. 6,303,374.

Oligonucleotides or polynucleotides of the present invention may also include base modifications or substitutions. As used herein, "unmodified" or "natural" bases include the purine bases adenine (A) and guanine (G) and the pyrimidine bases thymine (T), cytosine (C), and uracil (U). "Modified" bases include but are not limited to other synthetic and natural bases, such as: 5-methylcytosine (5-me-C); 5-hydroxymethyl cytosine; xanthine; hypoxanthine; 2-aminoadenine; 6-methyl and other alkyl derivatives of adenine and guanine; 2-propyl and other alkyl derivatives of adenine and guanine; 2-thiouracil, 2-thiothymine, and 2-thiocytosine; 5-halouracil and cytosine; 5-propynyl uracil and cytosine; 6-azo uracil, cytosine, and thymine; 5-uracil (pseudouracil); 4-thiouracil; 8-halo, 8-amino, 8-thiol, 8-thioalkyl, 8-hydroxyl, and other 8-substituted adenines and guanines; 5-halo, particularly 5-bromo, 5-trifluoromethyl, and other 5-substituted uracils and cytosines; 7-methylguanine and 7-methyladenine; 8-azaguanine and 8-azaadenine; 7-deazaguanine and 7-deazaadenine; and 3-deazaguanine and 3-deazaadenine. Additional modified bases include those disclosed in: U.S. Pat. No. 3,687,808; Kroschwitz, J. I., ed. (1990), "The Concise Encyclopedia Of Polymer Science And Engineering," pages 858-859, John Wiley & Sons; Englisch et al. (1991), "Angewandte Chemie," International Edition, 30, 613; and Sanghvi, Y. S., "Antisense Research and Applications," Chapter 15, pages 289-302, S. T. Crooke and B. Lebleu, eds., CRC Press, 1993. Such modified bases are particularly useful for increasing the binding affinity of the oligomeric compounds of the invention. These include 5-substituted pyrimidines, 6-azapyrimidines, and N-2, N-6, and O-6-substituted purines, including 2-aminopropyladenine, 5-propynyluracil, and 5-propynylcytosine. 5-methylcytosine substitutions have been shown to increase nucleic acid duplex stability by 0.6-1.2° C. (Sanghvi, Y. S. et al. (1993), "Antisense Research and Applications," pages 276-278, CRC Press, Boca Raton), and are presently preferred base substitutions, even more particularly when combined with 2'-O-methoxyethyl sugar modifications.

It will be appreciated that an RNA molecule can be also generated using recombinant techniques.

To express an exogenous polynucleotide (i.e., to produce an RNA molecule), a nucleic acid sequence encoding the polynucleotide of the present invention (e.g., SEQ ID NOs: 1, 3, 5, 6 or 7) is preferably ligated into a nucleic acid construct. Such a nucleic acid construct includes a promoter sequence for directing transcription of the polynucleotide sequence in the cell in a constitutive or inducible manner.

Constitutive promoters suitable for use with the present invention are promoter sequences which are active under most environmental conditions and most types of cells such as the cytomegalovirus (CMV) and Rous sarcoma virus (RSV). Inducible promoters suitable for use with the present invention include for example the tetracycline-inducible promoter (Zabala M, et al., Cancer Res. 2004, 64(8): 2799-804).

The nucleic acid construct (also referred to herein as an "expression vector") of the present invention includes additional sequences which render this vector suitable for replication and integration in prokaryotes, eukaryotes, or preferably both (e.g., shuttle vectors). In addition, typical cloning vectors may also contain a transcription and translation initiation sequence, transcription and translation terminator and a polyadenylation signal.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Preferably, the promoter utilized by the nucleic acid construct of the present invention is active in the specific cell population transformed. Examples of cell type-specific and/or tissue-specific promoters include promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264, 166).

Various methods can be used to introduce the expression vector of the present invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Introduction of nucleic acids by viral infection offers several advantages over other methods such as lipofection and electroporation, since higher transfection efficiency can be obtained due to the infectious nature of viruses.

The miRNAs of this aspect of the present invention (or the expression vectors encoding same) may be administered to the patient per se or as part of a pharmaceutical composition, where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the miRNAs accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, inrtaperitoneal, intranasal, or intraocular injections.

Conventional approaches for drug delivery to the central nervous system (CNS) include: neurosurgical strategies (e.g., intracerebral injection or intracerebroventricular infusion); molecular manipulation of the agent (e.g., production of a chimeric fusion protein that comprises a transport peptide that has an affinity for an endothelial cell surface molecule in combination with an agent that is itself incapable of crossing the BBB) in an attempt to exploit one of the endogenous transport pathways of the BBB; pharmacological strategies designed to increase the lipid solubility of an agent (e.g., conjugation of water-soluble agents to lipid or cholesterol carriers); and the transitory disruption of the integrity of the BBB by hyperosmotic disruption (resulting from the infusion of a mannitol solution into the carotid artery or the use of a biologically active agent such as an angiotensin peptide). However, each of these strategies has limitations, such as the inherent risks associated with an invasive surgical procedure, a size limitation imposed by a limitation inherent in the endogenous transport systems, potentially undesirable biological side effects associated with the systemic administration of a chimeric molecule comprised of a carrier motif that could be active outside of the CNS, and the possible risk of brain damage within regions of the brain where the BBB is disrupted, which renders it a suboptimal delivery method.

Alternately, one may administer the pharmaceutical composition in a local rather than systemic manner, for example, via injection of the pharmaceutical composition directly into a tissue region of a patient.

The term "tissue" refers to part of an organism consisting of an aggregate of cells having a similar structure and/or a common function. Examples include, but are not limited to, brain tissue and muscle tissue.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as crosslinked polyvinyl pyrrolidone, agar, or to alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuos infusion. Formulations for injection may be presented in unit dosage form, e.g., in ampoules or in multi-dose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (miRNA) effective to prevent, alleviate or ameliorate symptoms of a MND (e.g., ALS) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

The miRNAs may be administered alone or in conjunction with other known treatment methods. Thus, for example, the miRNAs of this aspect of the present invention may be administered together with Riluzole for the treatment of ALS.

Since, MNDs have been correlated with a decrease in activity and/or expression of miRNA-9 and/or miRNA-9*, the present inventors propose that identification of candidate agents for the treatment of a MND can be made on the basis of their ability to up-regulate miRNA-9 and/or miRNA-9*.

Thus, according to yet another aspect of the present invention there is provided a method of identifying an agent for the treatment of a MND, the method comprising:

(a) contacting a motor neuron with a candidate agent;

(b) assessing miR-9 or miR-9* activity or expression in the motor neuron; and (c) comparing the activity or expression in step (b) with an activity or expression in the absence of the candidate compound, wherein an up-regulation of activity or expression of miR-9 or miR-9* indicates that the candidate agent is a therapeutic agent for the treatment of MND.

The motor neuron may be isolated from any animal, including a mouse, a rat or a human. Alternatively, the motor neuron may be part of a motor neuron cell line—such as for example the murine motor neuron cell line, NSC19 [Smirnova IV Spine (Phila Pa. 1976). 1998 Jan. 15; 23(2): 151-8].

Yet alternatively, the motor neuron may be differentiated from a stem cell. According to one embodiment the stem cell is an embryonic stem cell (ESC). Such embryonic stem cells may be isolated from transgenic animals (e.g. mice) that serve as models for MNDs. For example embryonic stem cells may be isolated from a Tg(Hlxb9-GFP)1Tmj Tg(SMN2)89Ahmb Smn1$^{tm1Msd}$/J mouse (Jackson lab stock number 006570). Alternatively, embryonic stem cells may be isolated from transgenic animals, comprising a cholinergic-specific knockout of DICER. This model for MND is further described herein below.

Various methods are known for differentiation of embryonic stem cells into motor neurons, such as for example those described by Wichterle, H., et al., [Cell 110, 385-97 (2002)].

Exemplary candidate agents include small molecule agents, polynucleotide agents, chemicals, antibiotic compounds known to modify gene expression, modified or unmodified polynucleotides (including oligonucleotides), polypeptides, peptides, small RNA molecules and miRNAs.

It will be appreciated that the methods of contacting according to this aspect of the present invention typically depend on the type of candidate agent being tested. Thus, for example a polynucleotide agent is typically contacted with the motor neuron together with a transfection agent. A small chemical is typically placed in the motor neuron culture medium without additional agents.

To be considered a therapeutic agent, the candidate agents of the present invention typically up-regulate an activity or expression of miR-9 or miR-9* by at least 1.5 fold and more preferably by at least 2 fold.

Following selection of a candidate agent as a therapeutic agent for the treatment of an MND, the agent may be tested—for example on an animal model for the disease and ultimately the agent may be tested in humans. Validation of therapeutic efficacy may then lead to the preparation of the candidate agent as a pharmaceutical composition.

As mentioned, the present inventors have shown that transgenic animals comprising a cholinergic-specific knock-out of DICER may serve as live models for MNDs since they show, amongst other relevant phenotypes, a muscular atrophy compared to their corresponding wild-type mammals.

Thus, according to yet another aspect of the present invention there is provided a transgenic non-human mammal, comprising a cholinergic-specific knock-out of DICER, wherein the mammal exhibits muscular atrophy compared to a wild-type mammal.

As used herein, the term "DICER" refers to an endonuclease enzyme capable of cleaving long, double-stranded RNA molecules into fragments of 21-23 base pairs. Dicer is expressed from the gene AF430845 on mouse chr12:102,185,761-102,246,274).

A "transgenic animal" denotes a non-human animal, preferably a mammal chosen from among the rodents group and particularly the mouse, rat, hamster and guinea pig. The mouse is particularly appreciated because its immune system has been studied in detail. Alternatively, the transgenic animal is chosen from among bred animals and particularly from porcines, ovines, caprinae, bovines, equidae and particularly horses, and lagomorphs, particularly rabbits. The transgenic animal according to the invention can also be chosen from among primates, particularly monkeys such as the macaque, chimpanzee and the baboon.

The transgenic animals of the present invention can be categorized as "knockouts". A "knockout" has an alteration in the target gene via the introduction of transgenic sequences that results in a decrease of function of the target gene, preferably such that target gene expression is insignificant or undetectable.

According to one embodiment, the transgenic animals of the present invention comprise a deletion in at least part of the DICER gene, such that the protein encoded thereby, becomes non-functional. This can be achieved through random mutation (gene trap approach, chemical mutagenesis) or targeted insertion (homologous recombination).

According to one embodiment, the knock-out is mediated by Cre-loxP recombination.

According to this embodiment, the preparation of transgenic mammals that comprise a cholinergic-specific knock-out of DICER requires introduction of i) a polynucleotide encoding Cre operatively linked to a cholinergic specific promoter and ii) a polynucleotide encoding DICER flanked by lox-P sites into an undifferentiated cell.

Typically, such a cell is an embryonic stem (ES) cell. The transformed ES cell is then injected into a mammalian embryo, where it will integrate into the developing embryo. The embryo is then implanted into a foster mother for the duration of gestation.

Embryonic stem cells are typically selected for their ability to integrate into and become part of the germ line of a developing embryo so as to create germ line transmission of the heterologous gene construct. Thus, any ES cell line that has this capability is suitable for use herein. One mouse strain that is typically used for production of ES cells is the 129J strain. A preferred ES cell line is murine cell line D3 (American Type Culture Collection catalog no. CRL 1934). The cells are cultured and prepared for DNA insertion using methods well known in the art, such as those set forth by Robertson (Robertson, In: Teratocarcinomas and Embryonic Stem Cells: A Practical Approach, E. J. Robertson, ed., IRL Press, Washington, D.C., 1987).

Examples of cholinergic specific promoters include, but are not limited to the Vesicular Acetyl-Choline transporter promoter.

Typically, the transgenic animals generated according to this aspect of the present invention display symptoms of a MND. Such symptoms may include at least one of the following: sclerosis of the spinal cord ventral horns, aberrant end-plate architecture and muscular atrophy with signs of denervation.

It will be appreciated that the transgenic animals of this aspect of the present invention may be used to assay an effectiveness of a candidate agent for the treatment of a MND. Following administration of the candidate agent to the mouse, the motor functions of the mouse may be analyzed. If the motor functions improve, the candidate agent may be selected as a therapeutic agent and made up as pharmaceutical compositions.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", an and the include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Methods

Animals: Dicer gene was knocked-out specifically in post mitotic MNs by crossing a mouse carrying a Dicer conditional allele, to a Cre-recombinase transgene, driven by a cholinergic-specific promoter (Vesicular Acetyl-Choline transporter; VAChT-Cre). Mice were kept on a 12/12 h light/dark cycle, with food and water ad libitum. Mice were monitored for viability daily and weighed regularly.

Behavioral Examinations

Open field: The total distance traveled on a open-field apparatus consists of a white 120 lux illuminated Plexiglas box (50×50×22 cm) and the number of rearing events were quantified along a five minute test for each individual mouse, on three independent test sessions during the dark phase of the light-dark cycle, by an automated video tracking system (VideoMot2; TSE Systems, GmbH, Bad Homburg, Germany). For simplicity, data was normalized to the average of wild-type performance per time-point. However, a statistical analysis was performed on the data prior to normalization.

Vertical pole test: Mice were placed on a vertical rough-surfaced pole (diameter 2 cm; height 40 cm) facing the upper edge. The time taken to turn downwards and the time taken to descend the pole was measured. Data was averaged across three trials per mouse per time-point.

Home-cage locomotion: Mice were single-housed, and locomotive activity was examined automatically over a 48 hour period using the InfraMot system (TSE Systems, Bad Hamburg, Germany).

Electromyography: Mice were anesthetized with ketamine/xylazine i.p., and needle EMG was performed with a bipolar EMG needle electrode inserted in multiple sites into the hindlimb interosseous and gastrocnemius muscles. Recording was performed with a conventional EMG apparatus (Medelec, G B). For each mouse, EMG findings were graded on a 1-7 scale designated the "EMG Pathology Index" that reflects the intensity and frequency of fibrillation potentials. Representative screen captures of EMG traces were processed using Photoshop (Adobe).

Tissue preparation and staining: Mice were deeply anesthetized with chloral hydrate (1.4 µg/g body weight, i.p.) or Ketamine/xylasine (0.25 ml, 10% i.p.) and directly processed or transcardially-perfused with 10 ml of PBS, followed by 100 ml of 2.5% paraformaldehyde (PFA). Tissues were equilibrated in a mixture of 1.25% PFA and 15% sucrose for 24 hours. Spinal coronal 20 µm 'floating' sections were collected and stored in PBS at 4° C.

For lumbar perikaryon analysis, spinal cord sections were cresyl violet-stained and large (diameter larger than ~20 µm) Nissl-positive cells were counted and presented as mean number per ventral horn. Every 6th L2-L3 lumbar spinal cord section was used for counting (~15 sections per animal).

To detect Glial Fibrillary Acidic Protein (GFAP), free floating sections were pre-incubated in PBS solution containing 20% normal horse serum and 0.3% Triton X-100 for 1 hour and incubated overnight at room temperature with polyclonal rabbit anti-GFAP (1:200, Dako). Highly cross-absorbed cyanine2 (Cy2)-conjugated antibody against rabbit IgG (1:300, Jackson) was used for secondary detection. Image-Pro plus 4.1 software was used to quantify GFAP intensity in an oval region encompassing the lateral part of each ventral horn in 3 L2-lumbar sections per mouse.

Ventral and dorsal root processing and analysis: Ventral and dorsal roots were dissected at an L5 level with the dorsal root ganglion, fixed and embedded in paraffin. Antigen retrieval of re-hydrated 3 μm sections were submerged in citric acid and microwaved for 3 minutes. Tissues were blocked with 20% normal horse serum containing 0.2% triton X-100 for 1.5 hours and incubated overnight with polyclonal rabbit anti-heavy, medium or light neurofilament subunits (1:200, Novus Biologicals) together with rat anti MBP (1:50, Abcam). Sections were then washed with PBS and incubated for 45 minutes with Cy3-conjugated anti rabbit secondary antibody and Cy2 conjugated anti rat secondary antibody (1:200, Jackson). Digital florescent images of 0.08 and 0.5 mm$^2$ of the roots were collected on a E600 Nikon microscope (Nikon, Tokyo, Japan) equipped with Plan Fluor objectives and connected to a CCD camera (DMX1200F, Nikon). The mean density of individual axon staining and the number of axons in the roots were analyzed using Image-Pro plus 4.1 software.

Muscle and neuromuscular junction analysis: Medial gastrocnemius and tibialis anterior muscles were submerged in rhodamine-labeled bungarotoxin for five minutes (Molecular Probes; 1:200 in PBS), and then dissected out. Dissected muscles were rinsed in PBS, fixed in 1% PFA-PBS (pH 7.3) for 1 hour and equilibrated in 30% sucrose. 40 μm-thick muscle frozen-sections were incubated overnight in rabbit-raised polyclonal antibodies against neurofilament (Novus) or synaptophysin (Dako). Cy2 conjugated anti rabbit (1:200, Jackson) was used for secondary detection.

For angular fiber analysis, paraffin-embedded sections of the medial gastrocnemius and tibialis anterior muscles were stained with Hematoxylin and Eosin.

Differentiation of motor neurons and miRNA microarray: Mouse embryonic stem cells (mESCs) from a Tg(Hlxb9-GFP)1Tmj Tg(SMN2)89Ahmb Smn1$^{tm1Msd}$/J mouse (Jackson lab stock number 006570), were differentiated into motor neurons as previously described [Wichterle, H., et al., Cell 110, 385-97 (2002)]. Following dissociation of embryoid-bodies, GFP$^+$ motor neurons were purified via a MoFlo (Beckman Coulter) high speed cell sorter using a 100 μm nozzle at 30 psi. Motor neurons were plated on poly-d-lysine and laminin coated slides (BioCoat Cellware) and placed into wells facing a monolayer of primary mouse astroglial cells to provide trophic support.

Total RNA from motor neurons was extracted using TRO-Reagent (Ambion) according to the manufacturer's instructions. RNA integrity was evaluated using the Agilent 2100 bioanalyzer. Independent SMN1$^{mut}$ RNA samples and controls were labeled with a miRCURY Hy3/Hy5 labeling kit (Exiqon) according to the manufacturer's instructions. To avoid dye-associated bias, the experimental design involved reciprocation of the dye label in half of the samples. Hybridization onto a miRCURY LNA microarray slide (Exiqon) was followed by scanning on an Agilent DNA microarray scanner (Agilent Technologies). Following scanning of the microarrays, raw intensity data was extracted using SpotReader (Niles Scientific).

miRNA qRT-PCR expression analysis: Quantitative miRNA expression in derived motor neurons was acquired and analyzed using a Roche LightCycler 480 Real-Time PCR System (Roche Applied Science). Taqman microRNA assays for miR-9 and miR-9* (Applied Biosystems), were performed as previously described [Chen et al., Nucleic Acids Res 33, e179 (2005)]. The small RNA sno234 was used as internal control.

Cloning of 3' UTRs of neurofilament subunits and Onecut2: 3'UTR sequences of NFH (SEQ ID NO:8), NFM (SEQ ID NO:9), NFL (SEQ ID NO:10) and Onecut2 (SEQ ID NO:11) were PCR amplified from mouse genomic DNA. Mutated NFH 3' UTR sequence, lacking all miR-9 seed sequences, was synthesized with XbaI overhangs and inserted into PBluscript plasmid (Epoch Biolabs) (SEQ ID NO:12).

3'UTR fragments were ligated into pGem-T easy vector (promega) according to the manufacturer's guidelines, and further subcloned into XbaI site at the 3' end of luciferase in the pGL3-control destination vector (Promega). Cloning orientation was verified by diagnostic cuts and by sequencing.

Transfections and luciferase assay: HEK 293T cells grown on poly-1-lysine in 24-well format to a 70-85% confluency and transfected using Polyethyleneimine with the following plasmids: 20 ng of beta-galactosidase plasmid, 10 ng of pGL3-control-3'UTR plasmid and 430 ng of miR-9 or empty-miR-vec overexpression plasmids. Data from the Firefly luciferase assay (Promega) conducted 48 hours after transfection, were normalized to beta galactosidase levels and averaged across six well repetitions per condition.

Statistical analysis: Results were expressed as mean±standard error (SE). Student's t-test was used for the comparison of two groups. Statistics were performed using SPSS software (SPSS Inc., Chicago). For miRNA array data, analysis was performed using the Limma package from the Bioconductor project (http://wwwdotbioconductordotorg). LOESS normalization was applied within arrays and Aquantile normalization between arrays. Standard quality control was performed using the plot functions of Limma.

Example 1

Loss of miRNA Activity in the MNDicer$^{mut}$ Causes Progressive Kinetic Dysfunction In order to evaluate the involvement of miRNA in motor neuron (MN) pathologies, the present inventors specifically ablated Dicer 1 in post-mitotic, postnatal MNs, crossing a Dicer1 conditional allele to a Cre-recombinase transgene, driven by a cholinergic-specific promoter that is expressed in post-mitotic but not developing MNs (Vesicular Acetyl-Choline Transporter; VAChT-Cre). As Dicer activity is required for miRNA processing in vivo, VAChT-Cre;Dicer$^{flx/flx}$ animals (also referred to below as "MNDicer$^{mut}$") lose the ability to make functional miRNAs in a subset of postmitotic somatic MNs and therefore provide a compelling model for miRNA-loss of function in MNs.

Whereas VAChT-Cre;Dicer$^{flx/+}$ heterozygous animals ("controls") are apparently normal, MNDicer$^{mut}$ mice display a significantly shorter life expectancy and progressively lose weight (FIGS. 1A-B). To better understand the pathology of these mice, a broad series of functional tests was conducted to evaluate their kinetic activity. From the age of two months, the MNDicer$^{mut}$ mice were inferior to controls on a 'vertical pole test' (FIG. 1C). Video-monitored 'open-field' assay revealed that, MNDicer$^{mut}$ mice progressively travel shorter distances and rear less than controls (FIGS. 1D-E). Further, a home cage study across the circadian cycle, using the Infra-Mot system, indicated that MNDicer$^{mut}$ locomotor activity gradually deteriorates compared to controls (FIGS. 1F-H). It may be hypothesized that this apparent deterioration in physical strength is likely the consequence of muscular atrophy.

Example 2

The MNDicer$^{mut}$ Exhibits Denervation Muscular Atrophy

To directly characterize the muscle phenotype, an electromyographic (EMG) study was performed, which showed frequent fibrillation potentials. These data are consistent with an ongoing denervation process, which probably underlies the muscular atrophy (FIGS. 2A-B). MNDicer$^{mut}$ also exhibit angular myofibers on muscle histology, a pathognomonic sign of denervation-related muscular atrophy (FIG. 2C) and tremor that may also be attributed to denervation (data not shown). Taken together, it may be concluded that MNDicer$^{mut}$ animals suffer from denervation muscular atrophy, which suggest loss of MNs.

Example 3

Motor Neurons are Lost in the MNDicer$^{mut}$

A decrease in large perikaryon numbers (>20 μm diameter) in the ventral horn of the lumbar spinal cord (Nissl staining, FIGS. 3A-C) was observed by spinal cord histology. Negative immunoreactivity for both TUNEL and for activated-caspase-3 (data not shown), is consistent with a typical slow-death profile of MNs, encountered in many motor neuron diseases (MNDs). Reactive astrocytosis is often taken as an indication of neuronal toxicity or neuronal death, therefore glial fibrilary acidic protein (GFAP) expression levels were quantified on sections of lumbar spinal cords. Enhanced GFAP immunoreactivity was observed in the latero-ventral aspect of the MNDicer$^{mut}$ lumbar spinal cord sections, implying reactive-astrocytosis and further supporting MN loss (FIGS. 3D-F).

Example 4

Signs of "Dying Back" Axonopathy in the MNDicer$^{mut}$

Dysfunction and/or degeneration of the neuromuscular junction (NMJ) accompanies or even precedes the loss of motor neuron bodies in a few models of ALS. The present inventors therefore proceeded to evaluate potential distal axonal defects in the MNDicer$^{mut}$. At the age of four months, aberrant end-plate architecture was twice as frequent in the neuromuscular junctions of the Tibialis muscle in MNDicer$^{mut}$ mice relative to controls (FIG. 3G-M). These data imply that motor neuron dysfunction can be documented in live axons of MNDicer$^{mut}$ mice, similar to previously-observed "dying back" pathophysiology in other MND models. This is intriguing, because miRNAs are known to have distal, peri-synaptic function, suggesting that an early-onset, miRNA-related, neuropathy may precede the perikaryal death in the Dicer model. Accordingly, a discrete population of proximal motor axons at the ventral root were evaluated, before they are joined by sensory axons. MNDicer$^{mut}$ mice exhibited a significant decrease in MN axons when compared to controls, whereas dorsal root sensory axons remained intact (FIGS. 3N-P).

Example 5

MNDicer$^{mut}$ Fail to Coordinate Neurofilament Subunit Stoichiometry

Dysregulation of the coordinated expression of the light, medium and heavy neurofilament (NF) subunits (NEFL, NEFM, NEFH, respectively), causes axon cytoskeletal defects. For example, NEFL mutations cause type 2E Charcot-Marie-Tooth motor neuropathy. Further, experimental perturbation of fine neurofilament balance in mouse models, lead to phenotypes closely resembling human motor neuron pathologies and was previously suggested as a component of human ALS.

More specifically, posttranscriptional regulation of neurofilament gene expression plays a key role in neuronal well-being and deletion of the NEFH tail was suggested as a component of amyotrophic lateral sclerosis.

NF expression is regulated by the 3' untranslated region (3'UTR) of the mRNA, which appears to interact with an uncharacterized trans-acting factor that is attenuated in ALS [Ge et al., J Biol Chem 278, 26558-63 (2003)]. Relative expression levels of the NF subunit proteins were analyzed in MNDicer$^{mut}$ mice and sibling controls. Quantification of the NF immunofluorescent signal in approximately two thousand lumbar axons, revealed that the expression levels of NEFL and NEFM, were comparable with the wild type. However, the expression of the heavy subunit (NEFH) is specifically up-regulated in the MNDicer$^{mut}$ (FIGS. 4A-C).

Example 6

Coordinated Expression of the Neurofilament Subunits is Achieved by miR-9

To assess the possibility of a miRNA involvement in the up-regulation of NEFH in the MNDicer$^{mut}$ mice, NF sequences were searched for potential miRNA binding sites. A single miR-9 binding site was found on the NEFL mRNA. In contrast, the NEFH mRNA harbors nine miR-9 binding sites, dispersed over the 3'UTR of NEFH mRNA and the 3' portion of the coding region (FIG. 4D). Importantly, the present inventors were able to demonstrate that the interaction of miR-9 with its potential target sites affects the NEFH mRNA in a heterologous reporter assay and that this depends on the presence of the seed binding sites (FIG. 4E). This data strongly suggests a model, where the loss of miR-9 expression or activity may result in de-repression of NEFH and subsequently in dysregulation of NF stoichiometry.

Example 7 miR-9 is Specifically Down-Regulated in a Model of Spinal Muscular Atrophy

To relate these results to the pathogenesis observed in other MND models, miRNA expression levels were profiled in a model of spinal muscular atrophy (SMA), a pediatric MND caused by mutations in the SMN1 gene. Notably, dysregulation of neurofilament expression, reminiscent of those observed in the Dicer 1 model was reported in SMN1 mutants and SMN1 is functionally engaged in miRNA-protein complexes in human cells. Embryonic stem cells harboring an SMN1 mutation into motor neurons were differentiated in vitro into motor neurons. Next, a miRNA microarray (LNA oligo platform, Exiqon) was screened with labeled RNA extracted from FACS-purified SMN1$^{mut}$ MNs. Direct comparison of RNA from wild-type and SMN1$^{mut}$ MNs revealed that the expression of only a few miRNA is significantly decreased in SMN1$^{mut}$ MNs. Intriguingly, the most significantly down-regulated miRNAs turned out to be miR-9 and miR-9* (FIG. 4F). These two miRNAs are processed from the same hairpin, and qPCR quantification revealed up to 15-fold decrease in their expression levels in SMN1$^{mut}$ MNs (FIG. 4G).

Taken together, the present inventors present a novel model for MND, based on Dicer 1 loss of function. In this model, MN-specific loss of miRNA activity results in denervation muscular atrophy. Additionally, changes in the expression levels of the neurofilament subunits likely contribute to the disease. This phenotype is attributed to dysregulation of miR-9, which resides upstream of the neurofilament mRNAs. miR-9 relevance to MNDs roots from its neuron-specific expression its dramatic downregulation in SMN1 deficient motor neurons.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of diagnosing a motor neuron disease (MND), the method comprising analyzing an activity or expression of miRNA-9 or miRNA-9* in a cerebrospinal fluid (CSF) sample or a blood sample of a human subject in need thereof, wherein a down-regulation of said activity or said expression of said miRNA-9 or miRNA-9* relative to said activity or said expression in a control sample of a healthy subject is indicative of the MND.

2. The method of claim 1, wherein the MND is selected from the group consisting of ALS, primary lateral sclerosis, progressive muscular atrophy, pseudobulbar palsy, progressive bulbar palsy, lower motor neuron disease and spinal muscular atrophy.

3. The method of claim 1, further comprising substantiating said diagnosis by measuring the extent of muscle involvement.

4. The method of claim 3, wherein said substantiating is effected by a test selected from the group consisting of transcranial magnetic stimulation (TMS), EMG, nerve conduction velocity study, laboratory screening, magnetic resonance imaging (MRI) and muscle or nerve biopsy.

5. The method of claim 3, wherein the MND is ALS.

* * * * *

SEQUENCE LISTING

```
<160> NUMBER OF SEQ ID NOS: 12

<210> SEQ ID NO 1
<211> LENGTH: 23
<212> TYPE: RNA
<213> ORGANISM: Homo sapiens
<220> FEATURE:
<221> NAME/KEY: misc_feature
<223> OTHER INFORMATION: miRNA-9

<400> SEQUENCE: 1
ucuuugguua ucuagcugua uga                                            23

<210> SEQ ID NO 2
<211> LENGTH: 22
<212> TYPE: RNA
<213> ORGANISM: Homo sapiens
<220> FEATURE:
<221> NAME/KEY: misc_feature
<223> OTHER INFORMATION: miRNA-9*

<400> SEQUENCE: 2
auaaagcuag auaaccgaaa gu                                             22

<210> SEQ ID NO 3
<211> LENGTH: 23
<212> TYPE: DNA
<213> ORGANISM: Artificial sequence
<220> FEATURE:
<223> OTHER INFORMATION: Exemplary miRNA-9 detecting oligonucleotide
      probe

<400> SEQUENCE: 3
tcatacagct agataaccaa aga                                            23

<210> SEQ ID NO 4
<211> LENGTH: 22
<212> TYPE: DNA
<213> ORGANISM: Artificial sequence
<220> FEATURE:
<223> OTHER INFORMATION: Exemplary miRNA-9* detecting oligonucleotide
      probe

<400> SEQUENCE: 4
actttcggtt atctagcttt at                                             22

<210> SEQ ID NO 5
```

```
<211> LENGTH: 89
<212> TYPE: RNA
<213> ORGANISM: Homo sapiens
<220> FEATURE:
<221> NAME/KEY: misc_feature
<223> OTHER INFORMATION: hsa-mir-9-1 precursor hairpin

<400> SEQUENCE: 5 cggggguuggu uguuaucuuu gguuaucuag cuguaugagu ggugugggagu cuucauaaag       60 cuagauaacc gaaaguaaaa auaacccca                                          89

<210> SEQ ID NO 6
<211> LENGTH: 87
<212> TYPE: RNA
<213> ORGANISM: Homo sapiens
<220> FEATURE:
<221> NAME/KEY: misc_feature
<223> OTHER INFORMATION: hsa-mir-9-2 precursor hairpin

<400> SEQUENCE: 6
ggaagcgagu uguuaucuuu gguuaucuag cuguaugagu guauuggucu ucauaaagcu        60
agauaaccga aaguaaaaac uccuuca                                            87

<210> SEQ ID NO 7
<211> LENGTH: 90
<212> TYPE: RNA
<213> ORGANISM: Homo sapiens
<220> FEATURE:
<221> NAME/KEY: misc_feature
<223> OTHER INFORMATION: hsa-mir-9-3 precursor hairpin

<400> SEQUENCE: 7
ggaggcccgu uucucucuuu gguuaucuag cuguaugagu gccacagagc cgucauaaag        60
cuagauaacc gaaaguagaa augauucuca                                         90

<210> SEQ ID NO 8
<211> LENGTH: 1206
<212> TYPE: DNA
<213> ORGANISM: Artificial sequence
<220> FEATURE:
<223> OTHER INFORMATION: Cloned NFH 3' UTR

<400> SEQUENCE: 8
ccctctagag gaggtaaaag ccaaagaacc cccaaagaag gtagaagaag agaagacact        60
gcctacacca agacagagg cgaaggagag taagaaagac gaagctccca aggaggcccc       120
gaagcccaag gtggaggaga agaaggaaac tcccacggaa aagcccaagg actctacagc      180
agaagccaag aaggaagagg ctggagagaa gaagaaagcc gtggcctcag aggaggagac      240
tcctgccaag ttgggtgtga aggaagaagc taaacccaaa gagaagacag agacaaccaa      300
gacagaagca gaagacacca aggccaaaga acctagcaaa cccacagaga cggaaaagcc      360
aaagaaagag gagatgccag cggcaccaga agagaaagac accaaggagg agaagaccac      420
agagtccagg aagcctgagg agaagcccaa aatggaggcc aaggtcaagg aggatgacaa      480 gagccttttcc aaagagccta gcaaacccaa gacagaaaag gctgaaaaat cctctagcac     540
agaccagaaa gaaagccagc ccccagaaaa gaccacagag gacaaggcca ccaagggaga      600
gaagtaagag aacaagagaa acacccagaa tagccaaaga aactcaggac ggtcccagta      660
ctcaggggtc ggcgtaataa attttatttc ttccttttccc tccgtaagaa gaaacactgc    720
ttagatggtg ggcctgccct caccaaacag gaatttctat taagattaag ttagcaagag      780
aagataaccc tgagccttgt ccccacgcc gaaaaccctc cccaggtgat ggacaattat       840
```

```
gatagcttct tgtagccgaa cgtgatgtat gctgaacgct acgcgtaaaa cacgcgtcta      900
aaaactgccc cctcctttcc aagtaagtgc atttatttcc tgtatgtcca actgacagat      960
gaccgcaata atgaatgagc agttagaaac gcattatgct tgaaatgttg taacctattc     1020
ctgaatgcct tcttgttttc caaggagtg gtcaggccct tgcccagtac acgctcctgg      1080
aagagctgca gcaggtgagg cagggcgctg ccactgaac cacgccaggg tgtactctcc      1140
actgaagtcc actttcaatt gcttccatgc aataaaacca agtgcttctg aaataaatct     1200
agaggg                                                                1206
```

<210> SEQ ID NO 9
<211> LENGTH: 509
<212> TYPE: DNA
<213> ORGANISM: Artificial sequence
<220> FEATURE:
<223> OTHER INFORMATION: Cloned NFM 3' UTR

<400> SEQUENCE: 9

```
ccctctagaa tcggagtccg ttgcaaaagg ttaagccata cgacaatttc aaaatgcatg       60
tgattgacag cttcaaaaca gaatgggttc tcccatgggg gctccagaca ttgtattttc      120
ctttgtgcaa tatgagggaa ctgcatgcaa gctcagggtg ccccctcct cagtccttgg      180 ggggaattca aatgcatgat cgtgtatgta cctagggaat tcgccagttt cctgagctgt      240
tggaagaggg gcactcgggg gggatgtctt gagatgtatt atgcagagta ccaactgagc      300 caaaataat aagtgaaaca gaactctctt agccttaaga aagctatata tgaatactta      360
cgtttacctc actggtgcat ttaaaatgga cttctgttca tgggagaacc ttgctgatct      420
gcacagttcg caaccttatc ttgatcgatg taaaatgtca cagcagtcct tgctcaataa      480
aggtcatact ggaaacataa tctagaggg                                         509
```

<210> SEQ ID NO 10
<211> LENGTH: 347
<212> TYPE: DNA
<213> ORGANISM: Artificial sequence
<220> FEATURE:
<223> OTHER INFORMATION: Cloned NFL 3' UTR

<400> SEQUENCE: 10

```
ccctctagaa gaagaaagat tgagccctat tcccaactat tccaggaaaa gttctcccca       60
atcaggtcaa cctcatcacc aaccaaccag ttgagttcca gatcctatac aaattaagaa      120
gtcaatacat gtataattct gagatgactt aggttggact ttcaatgttg tgctatgaat      180
ttcctcctta cgcagagtat ctgtttgctt gcagagtggc tttctggctt gctgccagcc      240
tgtgcatggt ccatgcttat gagttcagga tctatggcaa tgtgaatcac acagatgttt      300
acaataataa taaaaaaaaa accacacaca caacacgatc tagaggg                    347
```

<210> SEQ ID NO 11
<211> LENGTH: 1238
<212> TYPE: DNA
<213> ORGANISM: Artificial sequence
<220> FEATURE:
<223> OTHER INFORMATION: Cloned Onecut2 3' UTR

<400> SEQUENCE: 11

```
ccctctagac caaagaagca gaatactgca aaccaaagac atttgttacc tgccattttc      60
tagcctacaa atactgtgat tactttagc gatcagagca cctctgtaac tccgagtggc     120
attcggctct tgtcttgggc tcaccacctg gctgagcaga ccagctacat caatgacatt    180
agccaaatat ccgggcagtg acttcgccac gccagccctg gttggtcacc ttcccatagc    240
aagtgaaaga gggcccacag aactctggga gattacaaag gtcactatgt gcatatttac    300
cagtgaatgg ccccaggtgg gcaccaaggg gtgttcggag caagccaaaa gcttcgatga    360
ctctttacag acacttgaga ctgacttttg tatgaattgc ttaattgaaa ccaaagaaac    420
ttttttctg cacctacttc tgcaacaaac agaactgtcc cattgaatga gtaaatggtt     480
ccaccaatca ctggaaatca ccatcaacag aaaaagcacg ctagaatgaa agaaacaaca    540
aaaccaccga agacacactg tgttcaaaca gaccttttgg gacgctctta ttttttattt    600
ttttatttt tggaagcaga tttgaaagaa agggttgaga cacaaatcaa cagacgagcc     660
tcaatggctg ctgcttcata tgacaactca ctcggtaatc ttaacgttga agattgtctt    720
taatttgtgc ctatgcagtt tttcaaaaga acatggaaac agagcaacag aaacctcaac    780
agctacaata ccaaagatga ggattctcac acctttttgt ctcagttcat taccttcttt    840
tgcctggcta aaatacttat agcgtcattg atctgtacaa aggtaatcga ttttgtttct    900
ttaagcaaca aaaggaaagg gtcatttgtt tgattttatt gtttcccttt agttttgttt    960
tatggctttt acccaacatg gaatctcccc cctacacata aagttccatg gactccaaac   1020
ttgagatgtc gggatactga aaggtgtccc tttctctcct cagcagagca tgggaaatac    1080
gattgtcgct tgaatgtctg tggcttaacc cttagacttg gttgcttctg tgttcagtgt   1140
tgtcattagg ggagggaagg ggagcaagga tcaggggtag gagtctaggt gatccgccct   1200
ttccagaacc aaagaattta tagagaaatt ctagaggg                            1238
```

<210> SEQ ID NO 12
<211> LENGTH: 600
<212> TYPE: DNA
<213> ORGANISM: Artificial sequence
<220> FEATURE:
<223> OTHER INFORMATION: pBluescript cloning vector

<400> SEQUENCE: 12

```
gaatatctag agagaacaag agaaacaccc agaatagaac tcaggacggt cccagtactc      60
aggggtcggc gtaataaatt ttatttcttc ctttccctcc gtaagaagaa acactgctta    120
gatggtgggc ctgccctcac caaacaggaa tttctattaa gattaagtta gcaagagaag    180
ataaccctga gccttgtccc ccacgccgaa aaccctcccc aggtgatgga caattatgat    240
agcttcttgt agccgaacgt gatgtatgct gaacgctacg cgtaaaacac gcgtctaaaa    300
actgcccct cctttccaag taagtgcatt tatttcctgt atgtccaact gacagatgac     360
cgcaataatg aatgagcagt tagaaacgca ttatgcttga aatgttgtaa cctattcctg    420
aatgccttct tgttttgagt ggtcaggccc ttgcccagta cacgctcctg gaagagctgc    480
agcaggtgag gcagggcgct ggccactgaa ccacgccagg gtgtactctc cactgaagtc    540
cactttcaat tgcttccatg caataaaacc aagtgcttct gaaataaatc tagaaaacac    600
```